US009408770B2

(12) United States Patent
Hall

(10) Patent No.: US 9,408,770 B2
(45) Date of Patent: Aug. 9, 2016

(54) KNEE REHABILITATION DEVICE WITH MEASUREMENT ELEMENT

(71) Applicant: Promotus LLC, Draper, UT (US)

(72) Inventor: Jacob Randy Hall, Draper, UT (US)

(73) Assignee: Promotus LLC, Draper, UT (US)

( * ) Notice: Subject to any disclaimer, the term of this patent is extended or adjusted under 35 U.S.C. 154(b) by 0 days.

(21) Appl. No.: 14/213,174

(22) Filed: Mar. 14, 2014

(65) Prior Publication Data

US 2014/0207030 A1 Jul. 24, 2014

Related U.S. Application Data

(63) Continuation-in-part of application No. 13/048,861, filed on Mar. 15, 2011.

(60) Provisional application No. 61/314,135, filed on Mar. 15, 2010.

(51) Int. Cl.
*A61B 5/11* (2006.01)
*A61H 1/02* (2006.01)

(52) U.S. Cl.
CPC ........ *A61H 1/024* (2013.01); *A61H 2201/0161* (2013.01); *A61H 2201/1269* (2013.01); *A61H 2201/1642* (2013.01)

(58) Field of Classification Search
CPC ..................................................... A61B 5/1071
See application file for complete search history.

(56) References Cited

U.S. PATENT DOCUMENTS 1,066,190 A 7/1913 Ellilngsworth
1,336,695 A 4/1920 Gromes
1,590,499 A * 6/1926 Cozad .................. A61B 5/1071 33/1 R
2,413,053 A 12/1946 Kolarik
2,545,843 A * 3/1951 Henry ............................. 602/16

(Continued)

FOREIGN PATENT DOCUMENTS

EP 0350956 A2 1/1990
JP 2002-065770 A 3/2002
KR 10-2009-0022266 A 3/2009

OTHER PUBLICATIONS

International Search Report dated Nov. 28, 2011 from International Patent Application No. PCT/US2011/028575, filed Mar. 15, 2011.

(Continued)

*Primary Examiner* — Loan H Thanh
*Assistant Examiner* — Rae Fischer
(74) *Attorney, Agent, or Firm* — Workman Nydegger

(57) ABSTRACT

In one example, a rehabilitation device includes a first element having first and second spaced-apart, generally parallel elongate members having proximal and distal ends. A second element is rotatably coupled to the first element and includes first and second spaced-apart, generally parallel elongate members having proximal and distal ends. One of the first and second elements is angularly adjustable relative to the other. A measurement device includes a measurement element connected to one of the first and second elements and configured for rotation relative to one of the first and second elements, such that when the rehabilitation device is operably disposed with respect to a joint of a patient, the measurement element is arranged for contact with anatomy of the patient. Finally, a scale is disposed proximate the measurement element and indicates a position of the measurement element relative to another portion of the rehabilitation device.

25 Claims, 30 Drawing Sheets

(56) References Cited

U.S. PATENT DOCUMENTS

| | | | | |
|---|---|---|---|---|
| 4,252,111 | A | 2/1981 | Chao et al. | |
| 4,252,112 | A | 2/1981 | Joyce | |
| 4,485,808 | A | 12/1984 | Hepburn | |
| 4,494,534 | A | 1/1985 | Hutson | |
| 4,665,905 | A | 5/1987 | Brown | |
| 4,844,454 | A | 7/1989 | Rogers | |
| 4,848,326 | A | 7/1989 | Lonardo | |
| 4,905,677 | A | 3/1990 | Pecheux | |
| 5,236,333 | A | 8/1993 | Barba, Jr. | |
| 5,253,639 | A | 10/1993 | Johnston | |
| 5,306,230 | A | 4/1994 | Bodine | |
| 5,453,075 | A | 9/1995 | Bonutti et al. | |
| 5,509,894 | A | 4/1996 | Mason et al. | |
| 5,685,830 | A | 11/1997 | Bonutti | |
| 5,687,742 | A | 11/1997 | Johnson | |
| 5,855,538 | A | 1/1999 | Argabright | |
| 5,891,061 | A * | 4/1999 | Kaiser | 601/33 |
| 6,821,262 | B1 | 11/2004 | Muse et al. | |
| 6,962,570 | B2 | 11/2005 | Callanan et al. | |
| 7,207,960 | B2 | 4/2007 | Kenney | |
| 7,309,305 | B2 | 12/2007 | Nichols | |

OTHER PUBLICATIONS

International Preliminary Report on Patentability and Written Opinion dated Sep. 18, 2012 from International Patent Application No. PCT/US2011/028575, filed Mar. 15, 2011.

Office Action dated Mar. 14, 2013 from U.S. Appl. No. 13/048,861, filed Mar. 15, 2011.

Office Action dated Aug. 13, 2013 from U.S. Appl. No. 13/048,861, filed Mar. 15, 2011.

Office Action dated Oct. 8, 2015 from U.S. Appl. No. 13/048,861, filed Mar. 15, 2011.

U.S. Appl. No. 13/048,861, Jan. 16, 2015, Final Office Action.

Office Action dated Mar. 24, 2014 from U.S. Appl. No. 13/048,861, filed Mar. 15, 2011.

* cited by examiner

KNEE REHABILITATION DEVICE WITH MEASUREMENT ELEMENT

RELATED APPLICATIONS

This application is a continuation-in-part (CIP) of, and hereby claims priority to, U.S. patent application Ser. No. 13/048,861, entitled KNEE REHABILITATION DEVICE, and filed on Mar. 15, 2011 (the "'861 Application"). The '861 Application, in turn, claims priority to U.S. Provisional Patent Application No. 61/314,135, entitled KNEE REHABILITATION DEVICE, and filed on Mar. 15, 2010. All of the aforementioned applications are incorporated herein in their entireties by this reference.

BACKGROUND OF THE INVENTION

This invention relates generally to mechanical devices used to facilitate knee range of motion, which can be used in various stages of knee rehabilitation and more particularly, to an apparatus that can be used by a patient, with or without the aid of medical personnel, to engage in full joint flexibility following a knee impairment which can be used in multiple positions, by multiple methods, and multiple locations due to convenience of size and simplicity of use.

Medical patients who have undergone knee joint surgery, or have otherwise suffered joint impairment, typically require rehabilitative therapy so that an optimum range of motion can be achieved for the affected joint. The two most common knee surgeries are repair of the anterior cruciate ligament (ACL) and complete joint replacements. Over ten million such surgeries are performed worldwide, with over ten percent of that number occurring in the U.S., alone. Following knee surgery, it is imperative that the patient undergo rehabilitative therapy in order to recover full range of motion in the affected joint.

Patient compliance with therapeutic protocol is important in order to obtain full joint flexibility and function. Patient compliance with existing knee contracture correction devices and continuous passive motion devices tends to be low due to complexity, difficulty-of-use, and/or cost.

The present invention provides a simple, cost-efficient, comfortable, and easy-to-use solution. In addition there is no assembly of s bands required to attach the device to a lower extremity during a therapy session, as in Velcro (registered trademark), buckles, etc.

The present invention may also be used in many different positions, including supine, recumbent, or even standing and walking, and can be used in many different locations, including clinics, home, hospital, office, or even in water, as in a therapy pool or spa, or any other unique therapeutic environment.

As the therapy requires a significant amount of time and involves a certain amount of discomfort—particularly as the leg is extended—manual therapy devices, which are controlled by the patient are preferred. A number of manual devices have been developed over the years for facilitating rehabilitative therapy of the knee.

U.S. Pat. No. 6,962,570 to Keith E. Callanan, et al. describes a knee extension therapy apparatus for use by a patient in a recumbent position having the foot of his leg to be treated elevated to a level above the surface upon which the patient user is resting. The apparatus is equipped with a force translation pulley system, which subjects the knee to straightening forces when the patient pulls on a Cord. The apparatus can be collapsed for easy transport.

U.S. Pat. No. 6,821,262 to Richard R. Muse, et al. discloses a device for extending the leg of a patient following knee surgery. The device comprises an elongated member having a handle at one end, a harness for holding the patient's foot attached to the other end, and an adjustable slider assembly that can be positioned at a variety of locations along the elongated member. A fulcrum, which is attached to the slider assembly rests on top of the patient's leg, either above or below the knee, while the harness supports the patient's foot. The device is operated by the patient pulling on the handle, thereby straightening the leg, which increases the range of motion of the knee joint.

U.S. Pat. No. 5,855,538 to John Argabright discloses an exercise device that allows the use to extend each leg separately from a sitting position. A pair of upwardly curved tracks are affixed to horizontal base members by the rear support members and to vertical base members by the top support members. Tracks extend upwardly toward the forward end of the invention. The two foot plates are affixed to tracks by the foot plate attachment to move forward and rearward. A pair of foot supports are affixed to foot plates, wherein they can adjustably fit to a human being's feet as the legs are extended.

U.S. Pat. No. 5,685,830 to Peter M. Bonutti discloses an adjustable orthosis for stretching tissue by moving a joint between first and second relatively pivotal body positions. The orthosis includes a first arm with a cuff at its outer end to releasably attach the first arm to the first body portion. A second arm with a cuff at its outer end releasably attaches the second arm to the second body portion. The arms are pivotally interconnected by a connector section which is formed as one-piece with the first and second arms. An actuator is connected to the arms to apply force to the arms to pivot them relative to each other to move the joint. The actuator includes a flexible force transmitting member connected with at least one of the arms. A drive assembly is provided to tension the flexible force transmitting member and move the first and second arms relative to each other.

U.S. Pat. No. 5,509,894 to Bardley R. Mason, et al. discloses a leg suspension device for rehabilitative exercise of the leg, and specifically for passive or active range of motion exercise of the knee or hip joint. The device includes a bar having proximal and distal segments, and a fulcrum rotatably engaging the bar between the proximal and distal segments to permit rotation of the bar about the fulcrum in a vertical plane. Upper and lower leg cuffs are connected to the proximal and distal segments, respectively, suspending the thigh and leg while isolating the knee joint. A base is provided to free-standingly support the device during use, or, alternatively, the device is adapted for affixing to an overhead anchor. For passive motion exercise, the thigh and ankle are suspended from the cuffs and the user drives rotation of the bar solely with the upper body muscles about the fulcrum in alternate opposing directions, causing alternate passive flexion and extension of the knee and hip joint. The same procedure is repeated for assisted active motion exercise, but the user drives rotation of the bar about the fulcrum with the upper body and leg muscles simultaneously. For independent active motion exercise, the user drives rotation of the bar about the fulcrum entirely with the leg muscles.

U.S. Pat. No. 4,665,905 to Charles S. Brown discloses a pair of wire-frame structures, each of which is made of two parallel aligned members. Both wire-frame structures are joined by a pair of coil compression springs. A U-shaped yoke is adjustably affixed to each end of the aligned members. Each yoke is hinged to a cuff suitable for attachment to a human arm or leg by self-fastening bands. In use, the brace assemblage provides a dynamic tension to apply a controlled force on an elbow or knee flexion contracture.

U.S. Pat. No. 4,485,808 to George R. Hepburn discloses an adjustable splint assembly having upper and lower struts which are pivotally connected, with the pivotal connection incorporating a cam integral with one of the struts and a adjustable biasing mechanism within the other strut that applies a quantifiable force to the cam. The amount of force applied to the cam determines the torque required to flex the splint assembly at the pivotal connection. The splint is attached to a limb via hook and loop fasteners, with a pivotal axis of the limb joint (i.e., knee or elbow) being positioned coaxial with the pivotal axis of the splint's pivotal connection.

BRIEF SUMMARY OF SOME ASPECTS OF THE DISCLOSURE

The invention relates to a device for treating impairments in body joints from extension contracture, weakness in the supporting musculature, or some other malady in inhibiting the integrity of the body joint in accomplishing range of motion, weakness, or lack of full functionality. People develop extension contractures in knees and other joints from many and various causes. Weakness, disuse, fractures, surgeries, illness, and other causes have been known to cause loss of ability to flex the body joint otherwise known as an extension contracture.

The present invention provides several embodiments of a knee rehabilitation device, which can be used by an individual to assist the rotational component of the affected joint through its entire anatomical plane. It may be performed with or without the need of lower extremity muscle involvement. It is optimum to reduce lower extremity muscle recruitment in order to achieve a maximal stretch to the affected tissues related to the pathologic joint.

A first embodiment knee rehabilitation device is machined or cast from a lightweight structural metal, such as titanium, aluminum or magnesium. The device includes a generally U-Shaped handle of adjustable length that is rotatably coupled to a parallel-beam leg support. The leg support provides attachment points for an upper band that bridges the gap between the parallel beams and two pair of longitudinal slots, in which can slide a middle band and a lower band. The middle and lower bands also bridge the gap between the parallel beams. The lower band, which is used to support the leg beneath the ankle, slides within the lower of the two pair of longitudinal slots so that different leg sizes can be accommodated. The middle band, which fits over the anterior portion of the leg and inferior to the knee, can also be slid within the upper of the two pair of longitudinal slots. The adjustability of the middle band allows for different forces to be applied to the knee joint when a force is applied by the user of the device. The upper band, the position of which is non-adjustable, fits over the anterior portion of the leg either above or below the knee.

The U-shaped handle can be locked to the leg support at one of multiple positions throughout a range of rotation. It can make an acute angle, a right angle or an obtuse angle with the leg support. It can even be rotated to a storage position, whereby it makes essentially an angle of zero degrees with the leg support.

A second embodiment knee rehabilitation device, which is a variation of the first embodiment knee rehabilitation device, incorporates a rotatable support structure to which the upper and middle bands attach. The rotatable support structure enables the upper and middle bands to rotate independently of the leg support. The U-shaped handle can also be detached from the first and second embodiment knee rehabilitation devices and secured to a conventional post-operative knee brace that has been modified to include handle attachment hardware near the knee joint.

A third embodiment knee rehabilitation device includes a non-adjustable frame that is preferably fabricated entirely from a single piece of high-strength structural metal tubing. Structural metals include high-strength steel and stainless steel alloys, heat-treated aluminum, titanium and magnesium, and alloys thereof. A leg support portion of the device is formed by first and second spaced-apart parallel tube sections joined by a first U-shaped loop. The handle portion, formed by third and fourth spaced-apart parallel tubes joined by a second U-shaped look, makes an obtuse angle with the leg support portion, with which it is integral. Upper, middle and lower bands are coupled to the first and second parallel tubes and are slidable thereon for adjustability. The opposite ends of the single piece of metal tubing which forms the frame of the device are preferably joined in one of the U-shaped loop regions via either a butt-welded joint, or a brazed or adhesively-bonded sleeve joint.

A fourth embodiment knee rehabilitation device has a frame made of a pair of laminar sheet material components disposed in a mutually-parallel configuration, which can be a structural metal such as aluminum, steel alloys, stainless steel alloys, magnesium alloys and titanium. The laminar sheet material can also be a polymeric material, such as polyester thermoplastic resin that is reinforced by structural fibers such as para-aramid (e.g., Kevlar®), glass and carbon. Each of the frame components is reminiscent of a hockey stick or boomerang, with one end of each serving as a handle and the other serving as half of the leg support. Front, middle and rear bands bridge the gap between the two frame components. Each frame component is equipped with a pair of longitudinal slots, in tandem, in the leg support portion, which enables the front and middle band to adjustably slide back and forth in order to accommodate different sizes of patients and different therapy positions.

For any of the four embodiments of the knee rehabilitation device, the bands (also referred to as "bands" or "strap") can be made of durable cloth, a durable polymer such as polypropylene, leather, a composite sheet material (e.g., rubberized cloth), or some equivalent material.

BRIEF DESCRIPTION OF THE DRAWINGS

The appended drawings contain figures of some example embodiments to further clarify various aspects of the present disclosure. It will be appreciated that these drawings depict only some embodiments of the disclosure and are not intended to limit its scope in any way. The disclosure will be described and explained with additional specificity and detail through the use of the accompanying drawings in which.

DETAILED DESCRIPTION OF SOME EXAMPLE EMBODIMENTS

The present disclosure is generally concerned with therapy devices, one example of which is a knee rehabilitation device, that include a measurement device that enables ascertainment of the range of motion of an anatomical joint in connection with which the therapy device has been employed.

Figure 1A:
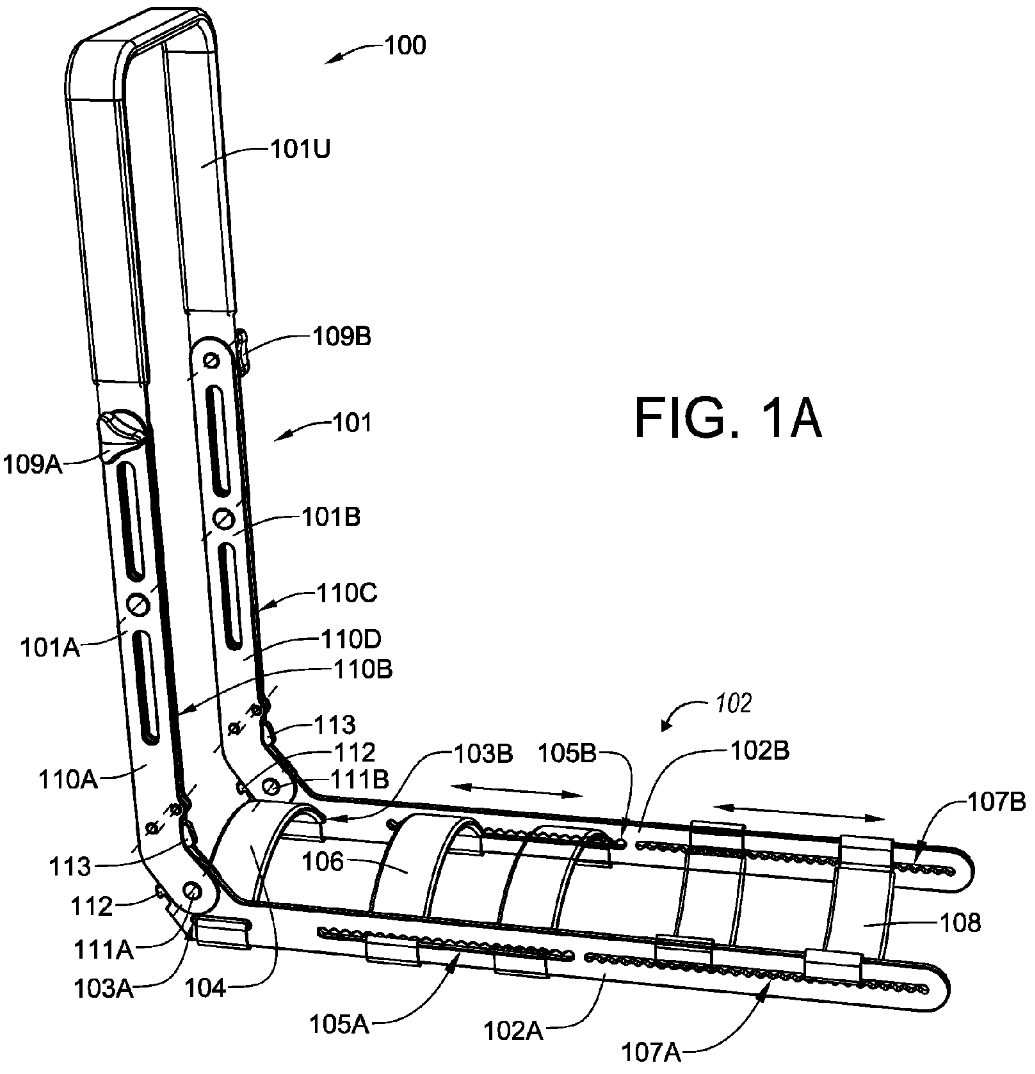
FIG. 1A is an isometric view of the first embodiment knee rehabilitation device showing how the middle band 106 and the ankle band 108 can be slidably moved to accommodate patients of different sizes.
Figure 1B:
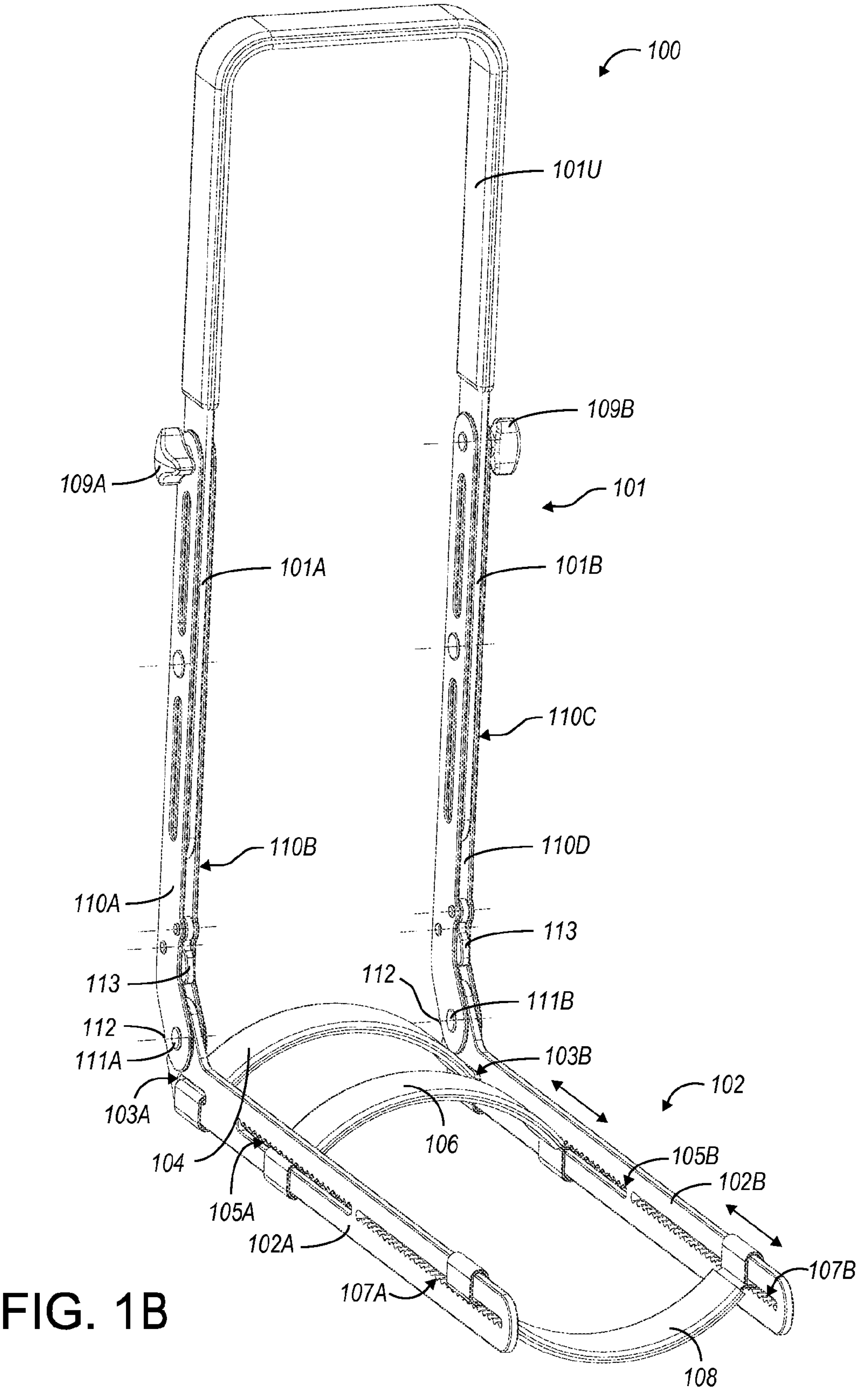
FIG. 1B is an isometric view of the device of FIG. 1B from a front perspective and shows the handle 101U slidably attached between members 110A and 110B and between 110C and 110 D.
Figure 2:
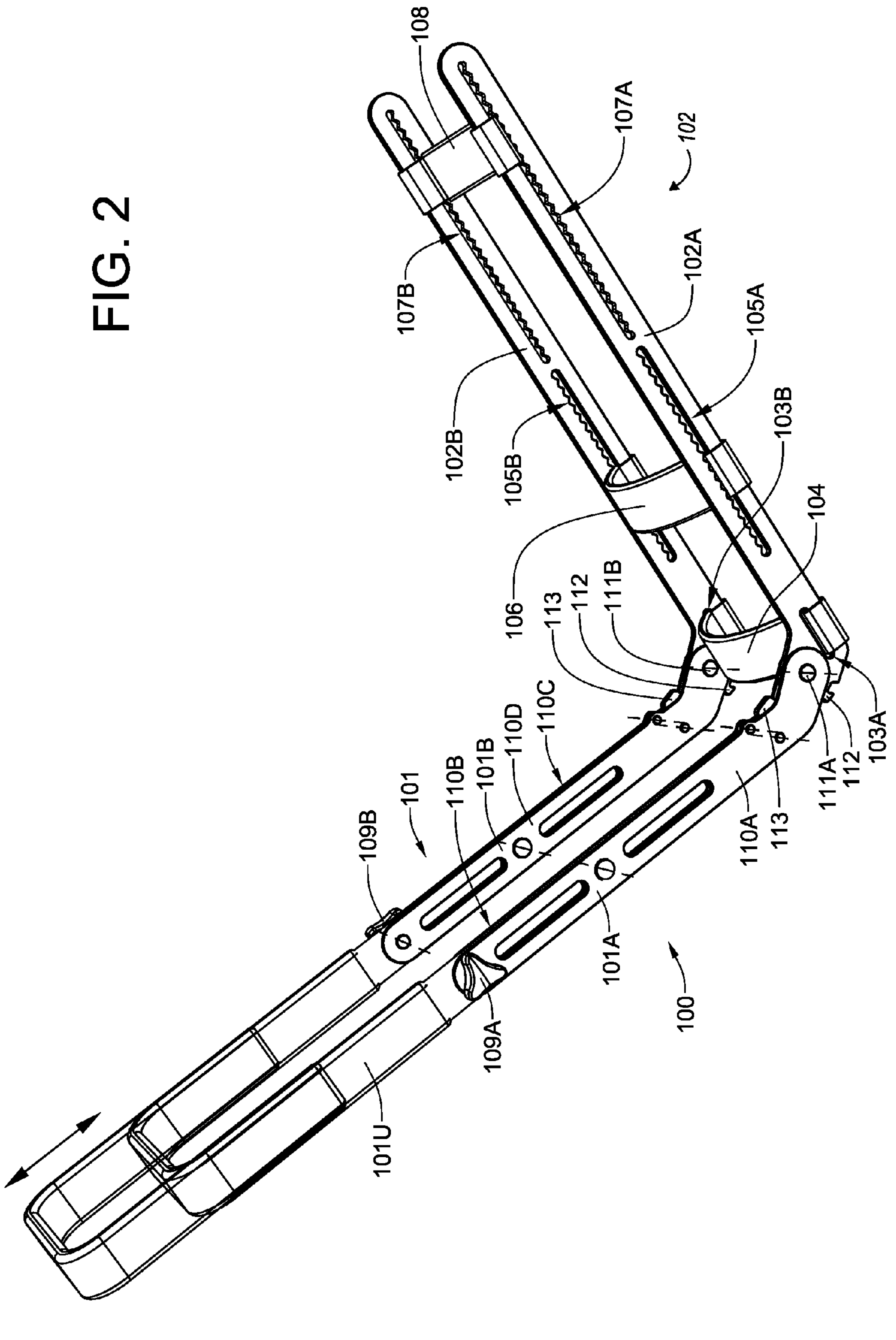
FIG. 2 is an isometric view of the first embodiment knee rehabilitation device also showing the handle length adjustment feature.

Referring now to FIGS. 1A, 1B and 2, a first embodiment knee rehabilitation device 100 is shown. Fabricated mostly of a lightweight structural metal, such as titanium, aluminum or magnesium or alloys thereof, the first embodiment knee rehabilitation device 100 includes a generally U-shaped handle 101 of adjustable length that is rotatably coupled to a parallel-beam leg support 102. The leg support 102 provides a pair of upper attachment slots 103A and 103B for mounting of an upper band 104 that bridges the gap between the parallel beams 102A and 102B, a first pair of elongated attachment slots 105A and 105B for mounting of a slidably-adjustable middle band 106, and a second pair of elongated attachment slots 107A and 107B for mounting of a slidably-adjustable lower band 108. The middle and lower bands 106 and 108, respectively, also bridge the gap between the parallel beams 102A and 102B. The lower band 108, which is used to support the leg beneath the ankle, slides within the lower of the second pair of longitudinal slots 107A and 107B so that different leg sizes and different injuries and/or surgical incisions can be accommodated. The middle band 106, which fits over the front of the patient's calf, can also be slid within the first, or upper pair of longitudinal slots 105A and 105B. The adjustability of the middle band 106 allows for different forces to be applied to the knee joint during therapeutic use, as well as accommodate injuries or surgical incision locations. Although the position of the upper band 104 is non-adjustable, it can be removed completely to accommodate certain therapy regimens. The upper band 104 fits over the front of the leg either just above or just below the knee, depending on the particular force desired during therapy. The U-shaped handle 101 has an upper portion 101U that is slidably coupled to a pair of lower extensions 101A and 101B. Threaded fasteners, but not limited to threaded fasteners, having a unitary knob 109A and 109B secure each side of the upper portion 101U to each of the lower extensions 101A and 101B, respectively. Lower extension 101A is constructed of two parallel, closely-spaced lower extension sub-members 110A and 110B, while lower extension 101B is constructed of identical lower extension sub-members 110C and 110D. The handle upper portion 101U slides between each pair of lower extension sub-members 110A and 110B or 110C and 110D, and the threaded fasteners 109A and 109B secure the handle upper portion 101U between each pair of lower extension sub-members 110A and 110B and lower extension sub-members 110C and 110D, respectively. Parallel beam 102A of the leg support 102 is coupled with a first hinge 111A to lower extension sub-members 110A and 110B, while parallel beam 102B is coupled with a second hinge 111B to lower extension sub-members 110C and 110D. Each hinge 111A and 111 B incorporates a notched locking disc 112 that is engaged by a pawl (not shown) that is actuated by release button 113.

Figure 3:
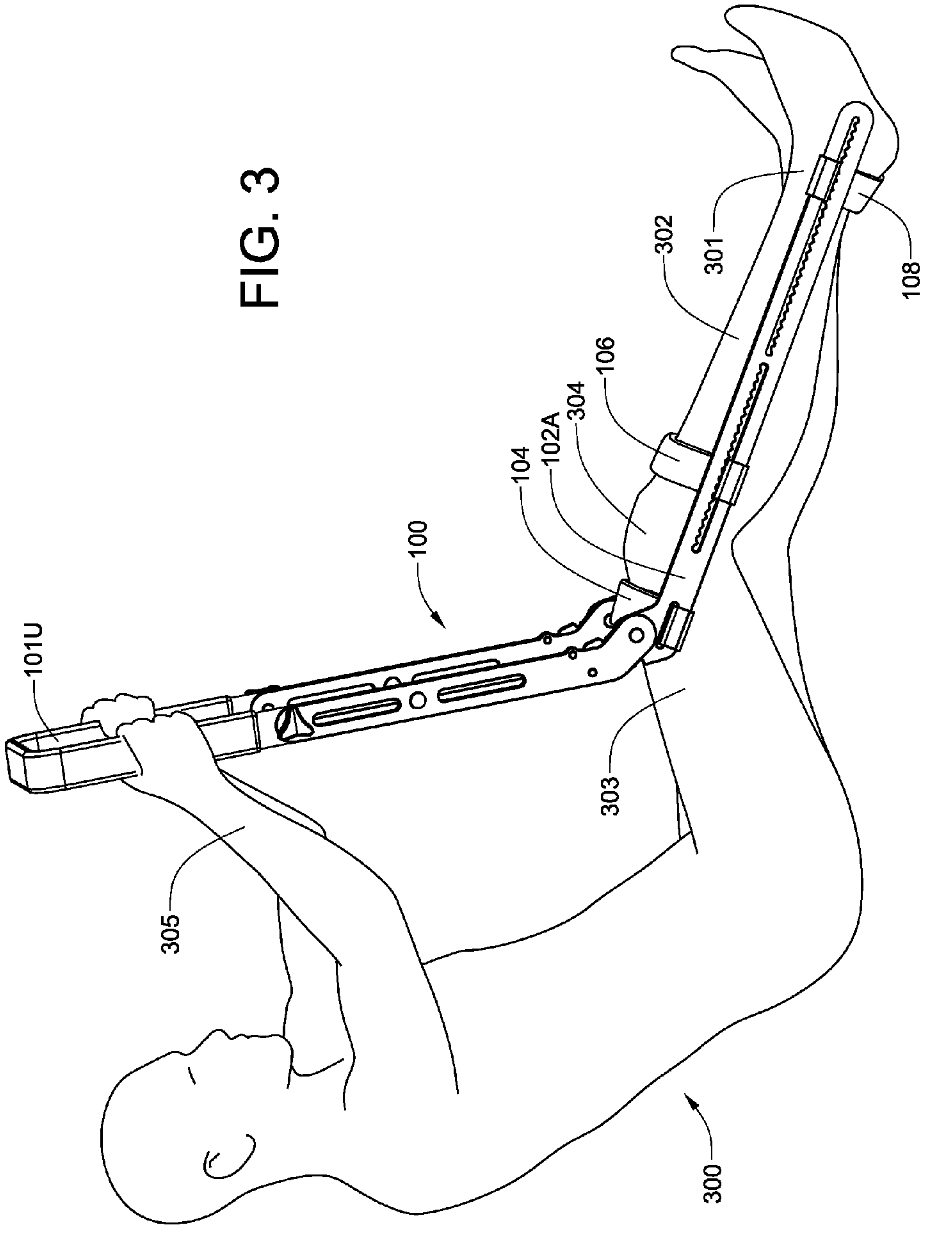
FIG. 3 is an isometric view of a first embodiment knee rehabilitation device being used by a patient.

Referring now to FIG. 3, the first embodiment knee rehabilitation device 100 is shown being used by a patient 300 in its standard operational mode.

Figure 4:
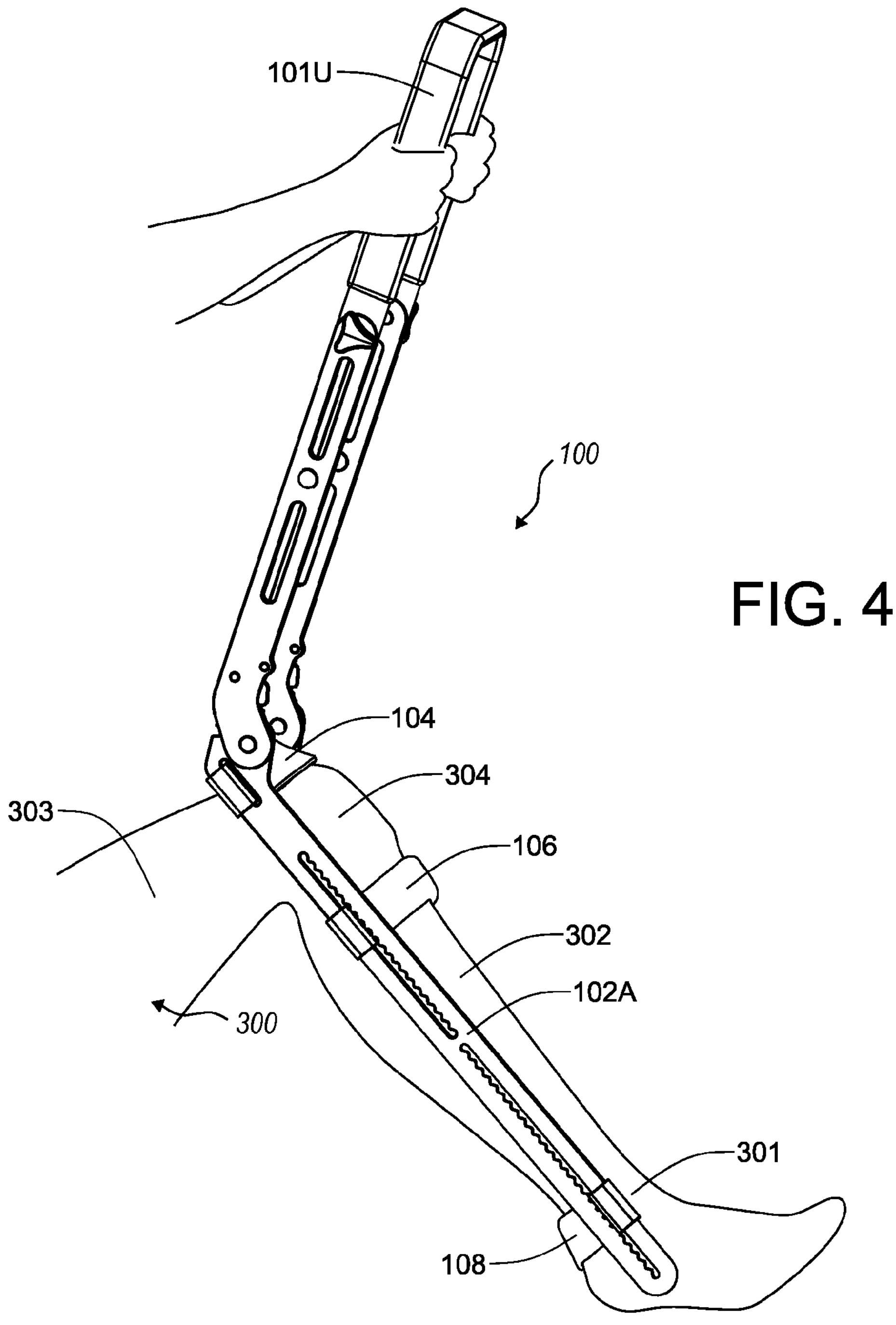
FIGS. 4, 5 and 6 show the first embodiment knee rehabilitation device being used by a patient to rotate his knee joint through various degrees of motion in FIGS. 4 and 5 to full extension in FIG. 6.
Figure 5:
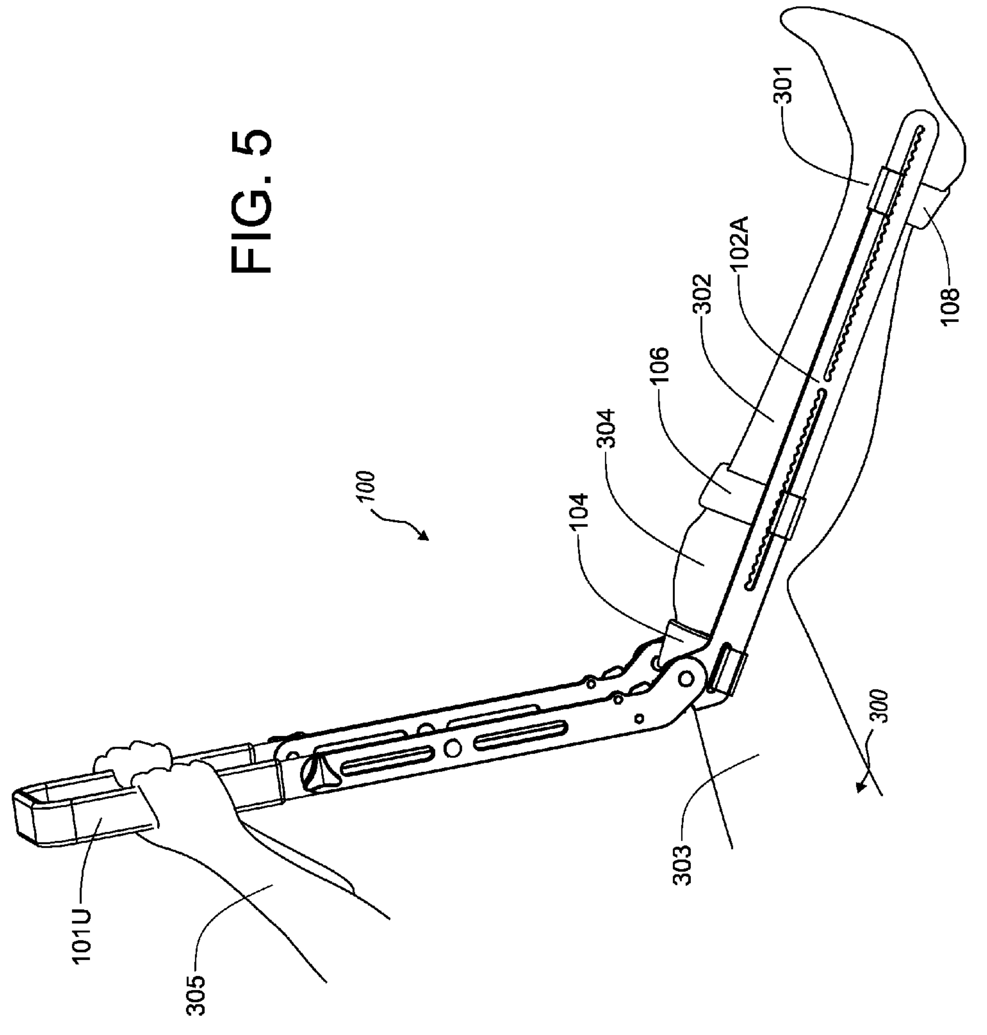
Figure 6:
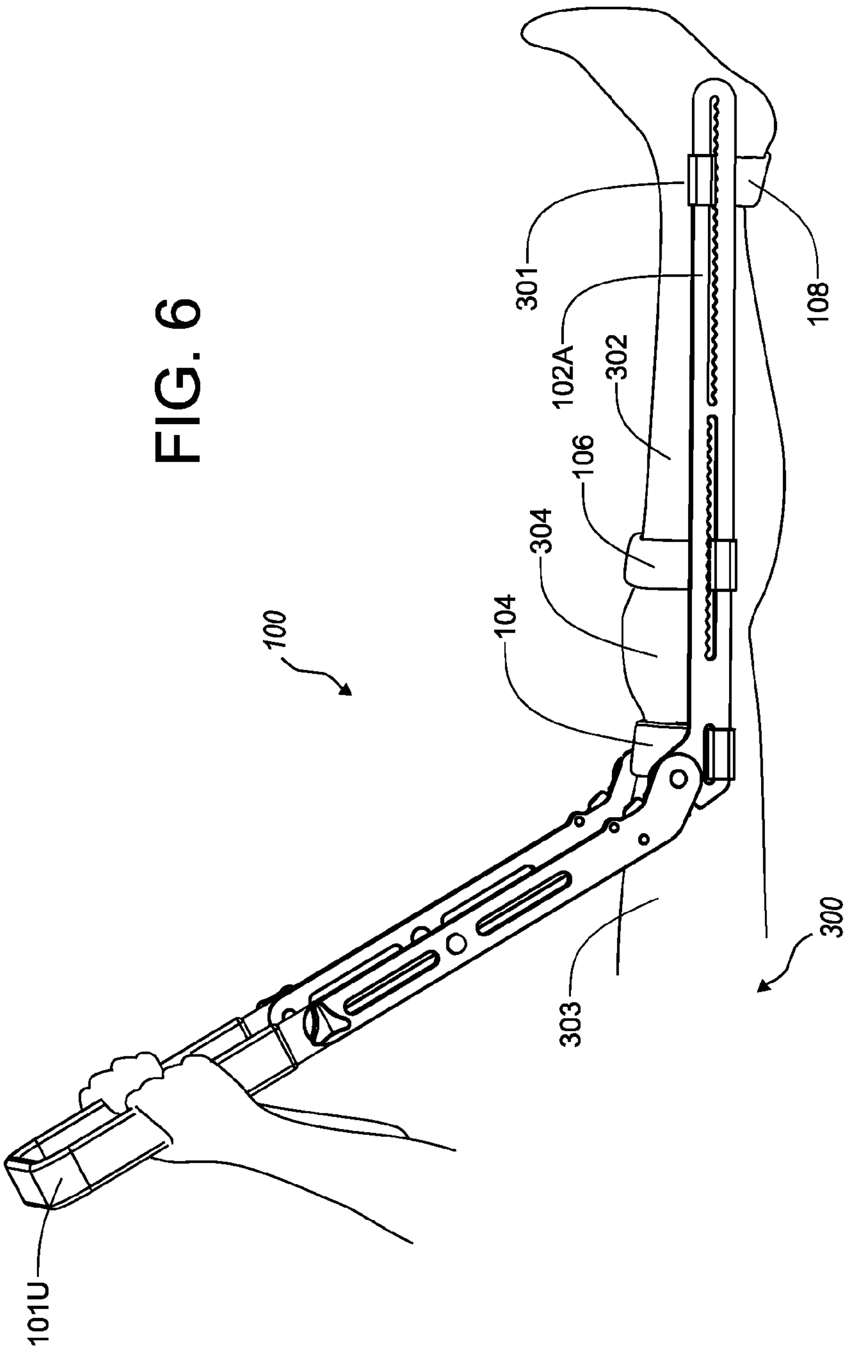

Referring now to FIGS. 4, 5 and 6, the first embodiment knee rehabilitation device 100 is being used by a patient 300 to rotate his knee 304 through various degrees of motion in FIGS. 4 and 5 to full extension in FIG. 6. It will be noted that for this therapy regime, the upper band 104 (also referred to as a band) is 15 positioned on the anterior portion of the thigh 303 just above the knee 304, the middle band 106 passes over the anterior portion of the lower leg 302 just below the knee 304, and the lower band 108 supports the lower leg 302 just posterior to the ankle 301. FIGS. 4, 5 and 6 show the first embodiment knee rehabilitation device in use by a patient 300 in its first, or standard, configuration, with the upper band 104 positioned just above the knee 304 on the anterior of the patient's thigh 303, the middle band 106 positioned on the anterior surface of the lower leg 302 just below the knee 304, and the lower band 108 positioned posterior to the ankle 301. In this First configuration, a moderate amount of pressure is applied to the knee 304.

Figure 7:
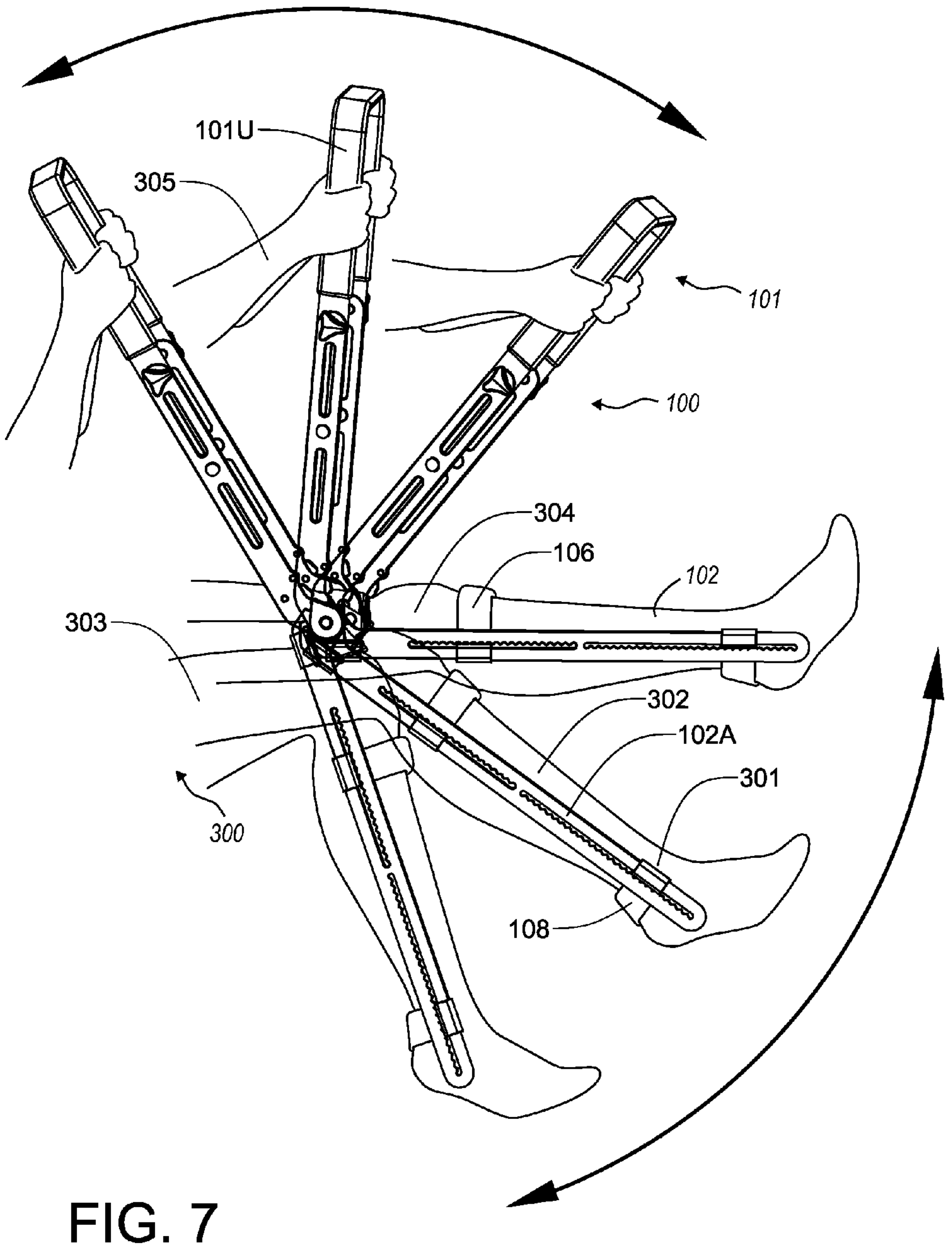
FIG. 7 is a right side elevational view of the first embodiment knee rehabilitation device being used by a patient, and showing how the device can be used for passive motion throughout the full range of joint motion.

Referring now to FIG. 7, the first embodiment knee rehabilitation device 100 is shown in use by a patient 300, as that patient moves the U-shaped handle 101, set on angular position B (see FIG. 9) with respect to the leg support 102, back and forth between positions of complete knee extension (represented by the horizontal leg configuration) and knee flexion (represented by the two non-horizontal leg configurations).

Figure 8:
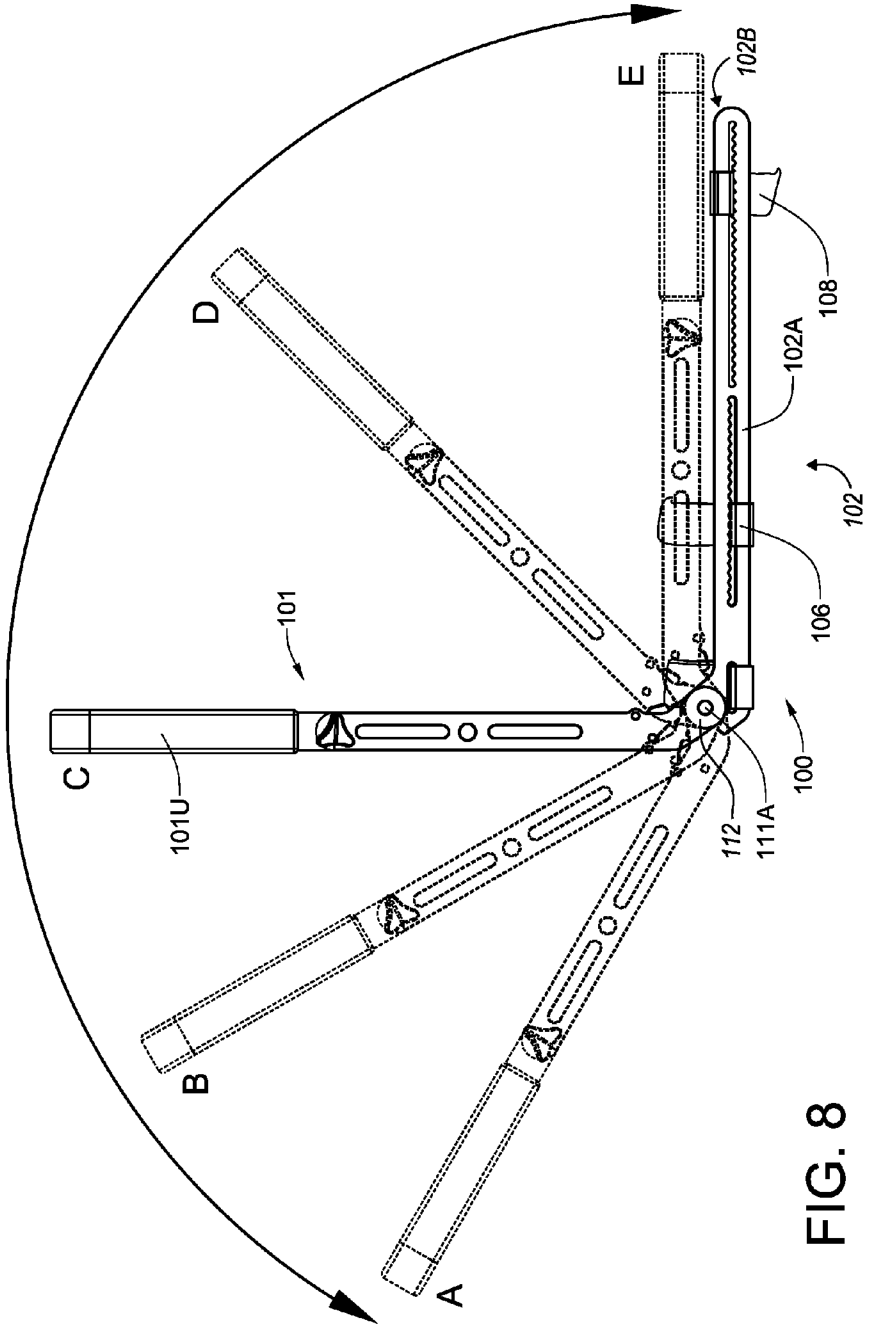
FIG. 8 is a side elevational view of the first embodiment knee rehabilitation device showing how the handle can be rotated and locked in a range of positions, including a completely folded position that can be used for storage.

Referring now to FIG. 8, each notched locking disc 112 provides a finite number of angularly-spaced lockable positions that the U-shaped handle 101 makes with the parallel beams 102A and 102B of the leg support 102. Five, but not limited to five, lockable angular positions A, B, C, D and E are shown in FIG. 6 8. Position E provides a compact device configuration for storage.

Figure 9:
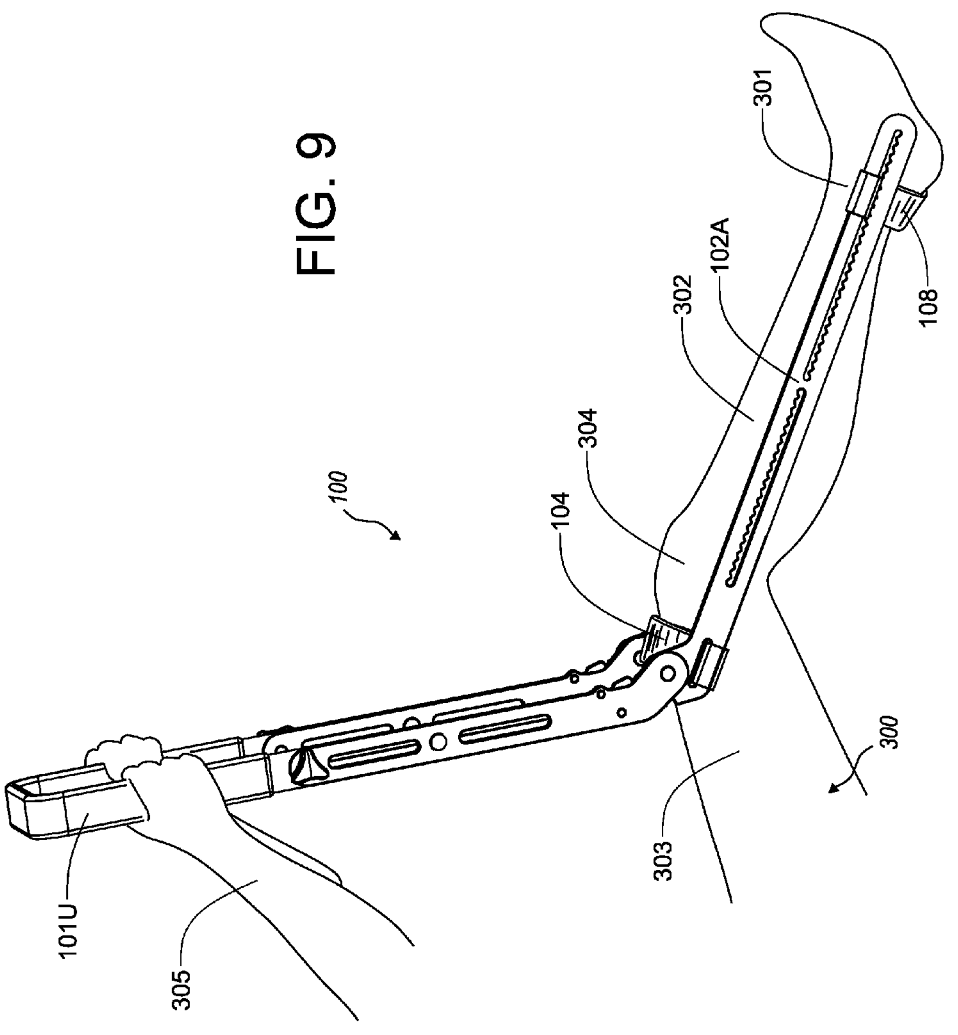
FIGS. 9, 10, and 11 show how the first embodiment knee rehabilitation device can be used with three other band configurations, each of which stretches the knee joint in a different way, with FIG. 9 showing the upper band positioned just superior to the knee, the middle band removed, and the lower band positioned posterior to the ankle, with FIG. 10 showing the upper band removed, the middle band positioned just inferior to the knee, and the lower band positioned posterior to the ankle, and FIG. 11 showing the upper band positioned just inferior to the knee, the middle band positioned inferior to the upper band and on the anterior portion of the leg, and the lower band positioned posterior to the ankle.

Referring now to FIG. 9, the first embodiment knee rehabilitation device 100 is shown in use by a patient 300 in a second configuration, with the upper band 104 positioned just above the knee 304 on the anterior of the patient's thigh 303, the middle band 106 (FIG. 8) removed, and the lower band 108 positioned posterior to the ankle 301. In this second configuration, minimum pressure is applied to the knee 304.

Figure 10:
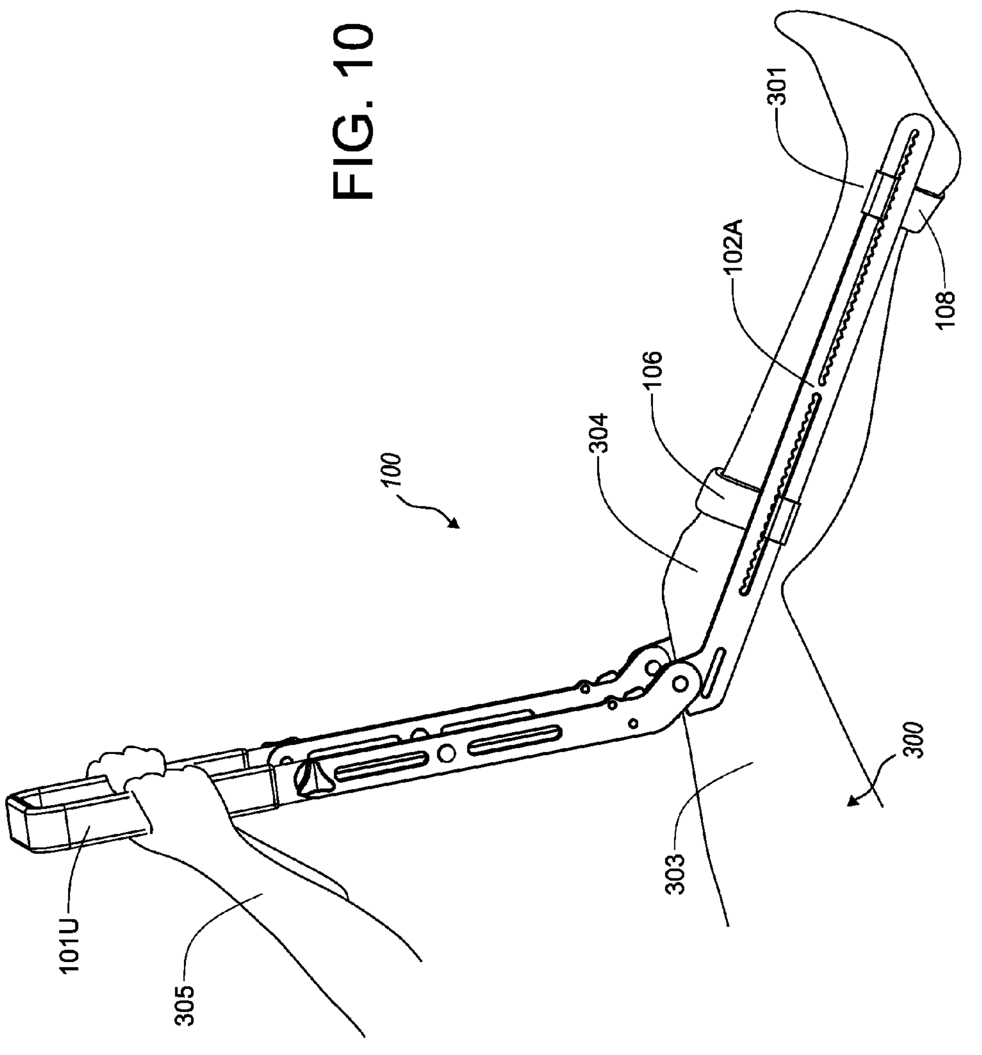

Referring now to FIG. 10, the first embodiment knee rehabilitation device 100 is shown in use by a patient 300 in a third configuration, with the upper band 104 (FIG. 9) removed, the middle band 106 positioned on the anterior surface of the lower leg 303 just below the knee 304, and the lower band 108 positioned posterior to the ankle 301. In this configuration, greater pressure is applied to the knee 304.

Figure 11:
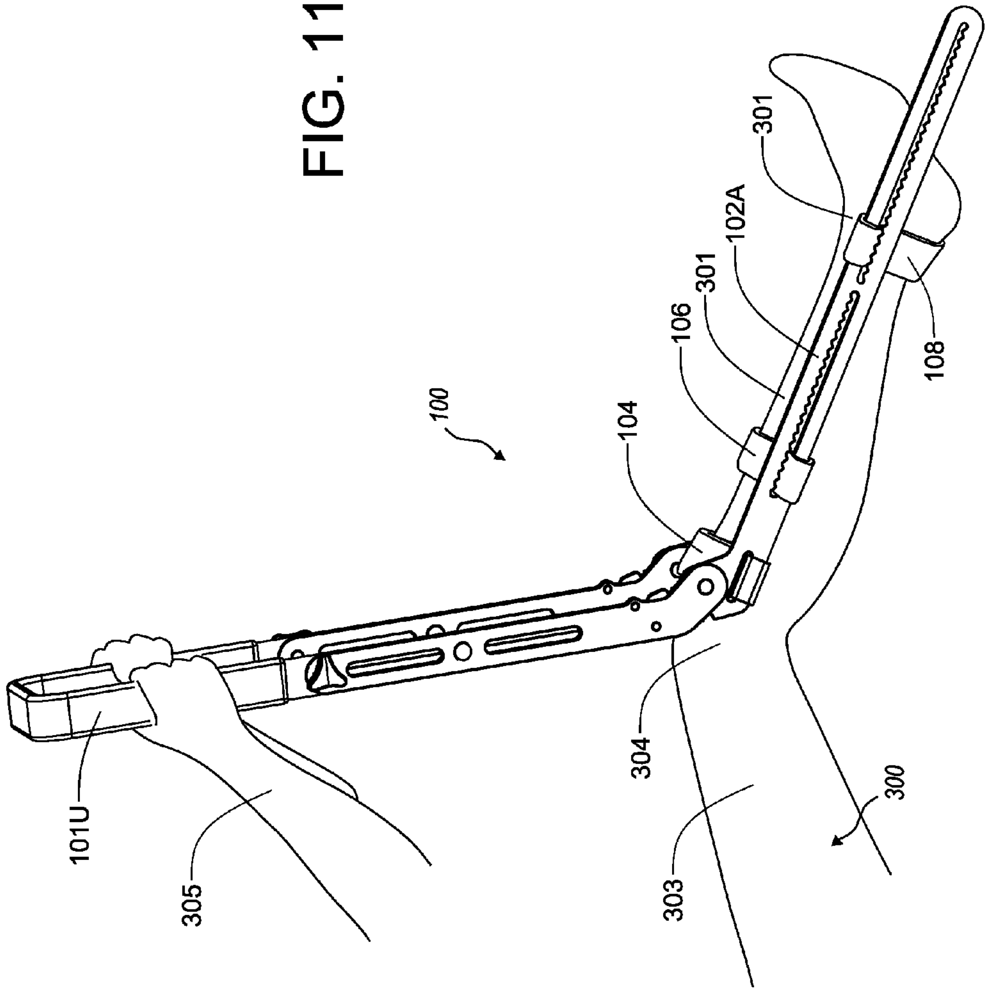

Referring now to FIG. 11, the first embodiment knee rehabilitation device 100 is shown in use by a patient 300 in a fourth configuration, with the upper band 104 positioned just below the knee 304 on the anterior surface of the patient's lower leg 303, the middle band 106 also positioned on the anterior surface of the lower leg 303 below the upper band 104, and the lower band 108 positioned posterior to the ankle 301. In this fourth configuration, pressure applied to the knee 304 is maximized during therapy sessions.

Figure 12:
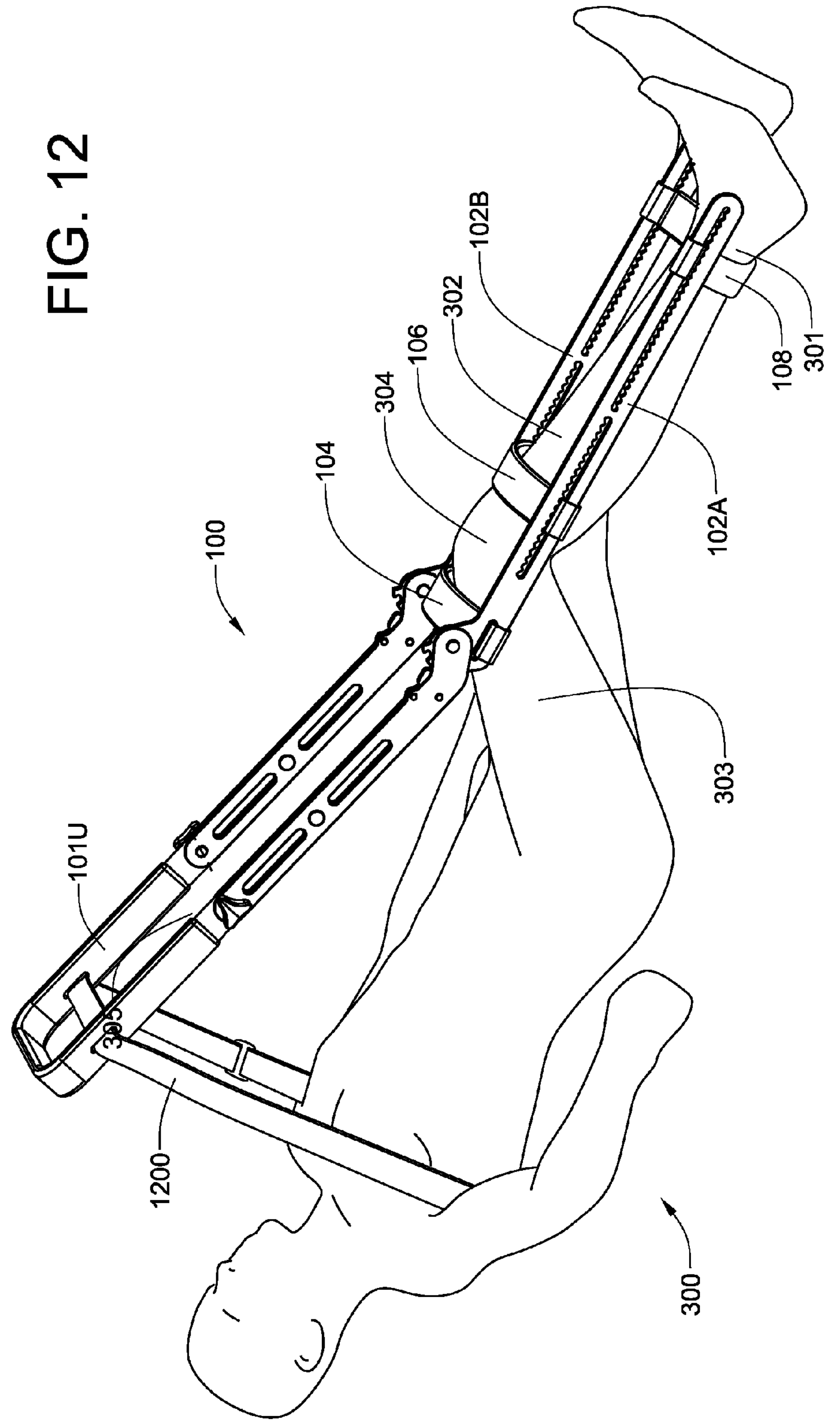
FIG. 12 is an isometric view of the first embodiment knee rehabilitation device being used by a patient in combination with a torso band.

Referring now to FIG. 12, is an isometric view of the first embodiment knee rehabilitation device 100 being used by a patient 300 in combination with a torso band 1200. The torso band 1200 can be employed to maintain a particular angle of flexion or extension of the leg being rehabilitated.

Figure 13:
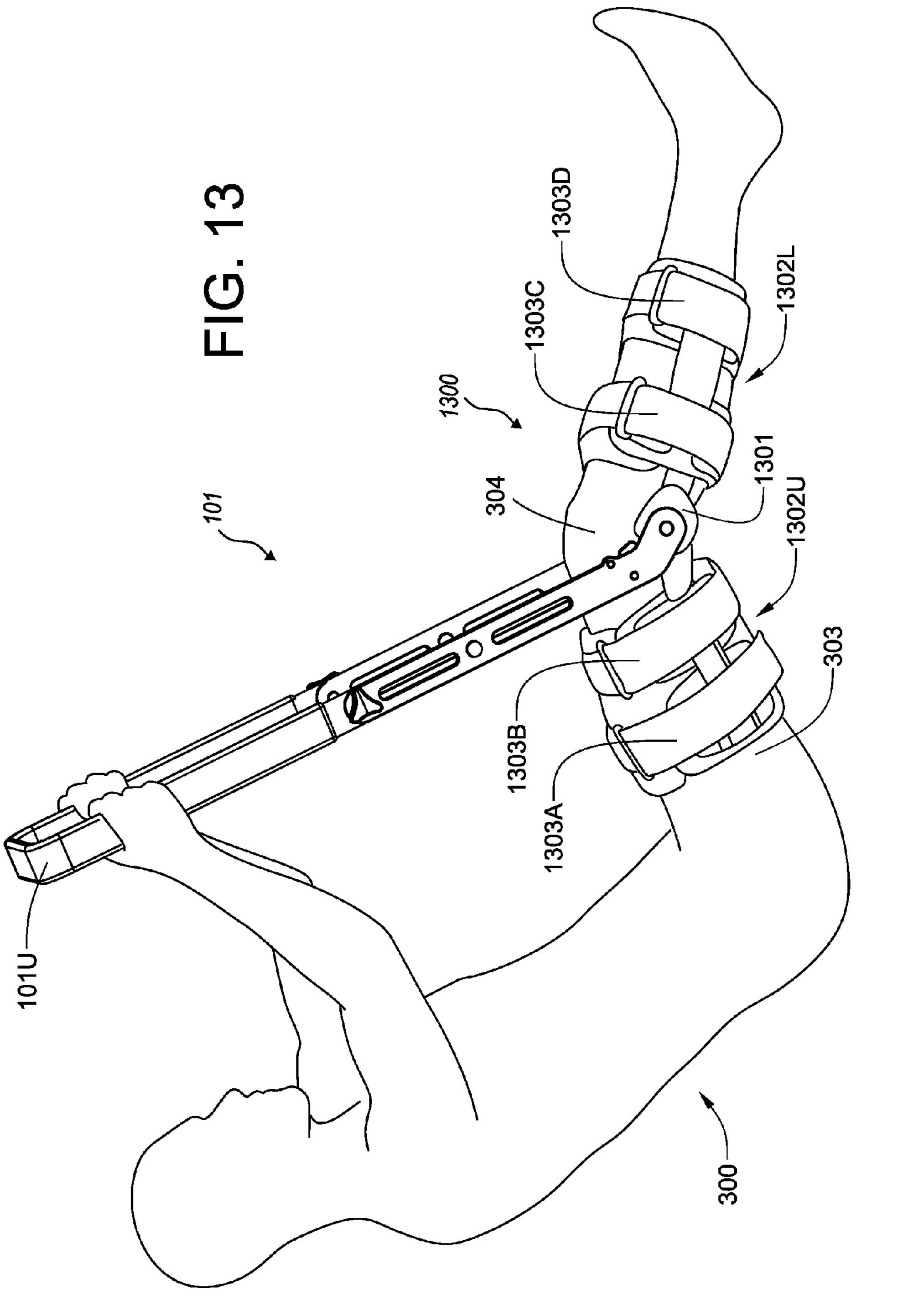
FIG. 13 is an isometric view of the handle of the first embodiment knee rehabilitation device being used by a patient in combination with a conventional knee brace that has been modified to include handle attachment hardware, as well a additional support structure and bands.

Referring now to FIG. 13, the U-shaped handle 101 of the first embodiment knee rehabilitation device 100 is shown being used by a patient 300 in combination with a conventional knee brace 1300 that has been modified to include handle attachment hardware 1301, as well as additional support structure (1302U and 1302L), and bands 1303A-1303D.

Figure 14:
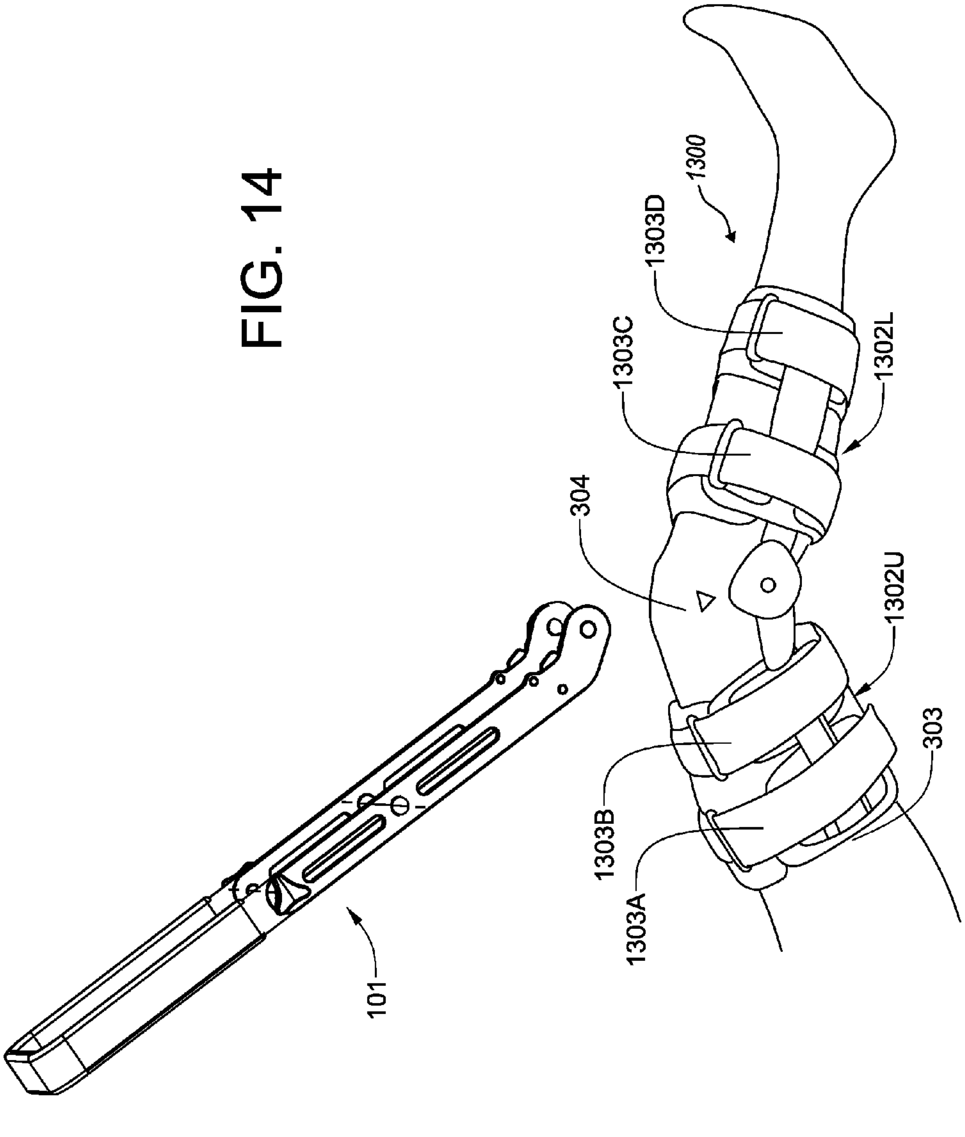
FIG. 14 is an isometric view of the assembly of FIG. 13, with the handle removed from the knee brace.

Referring now to FIG. 14, the assembly of is an isometric view of the assembly of FIG. 13, with the handle 101 removed from the knee brace 1300.

Figure 15:
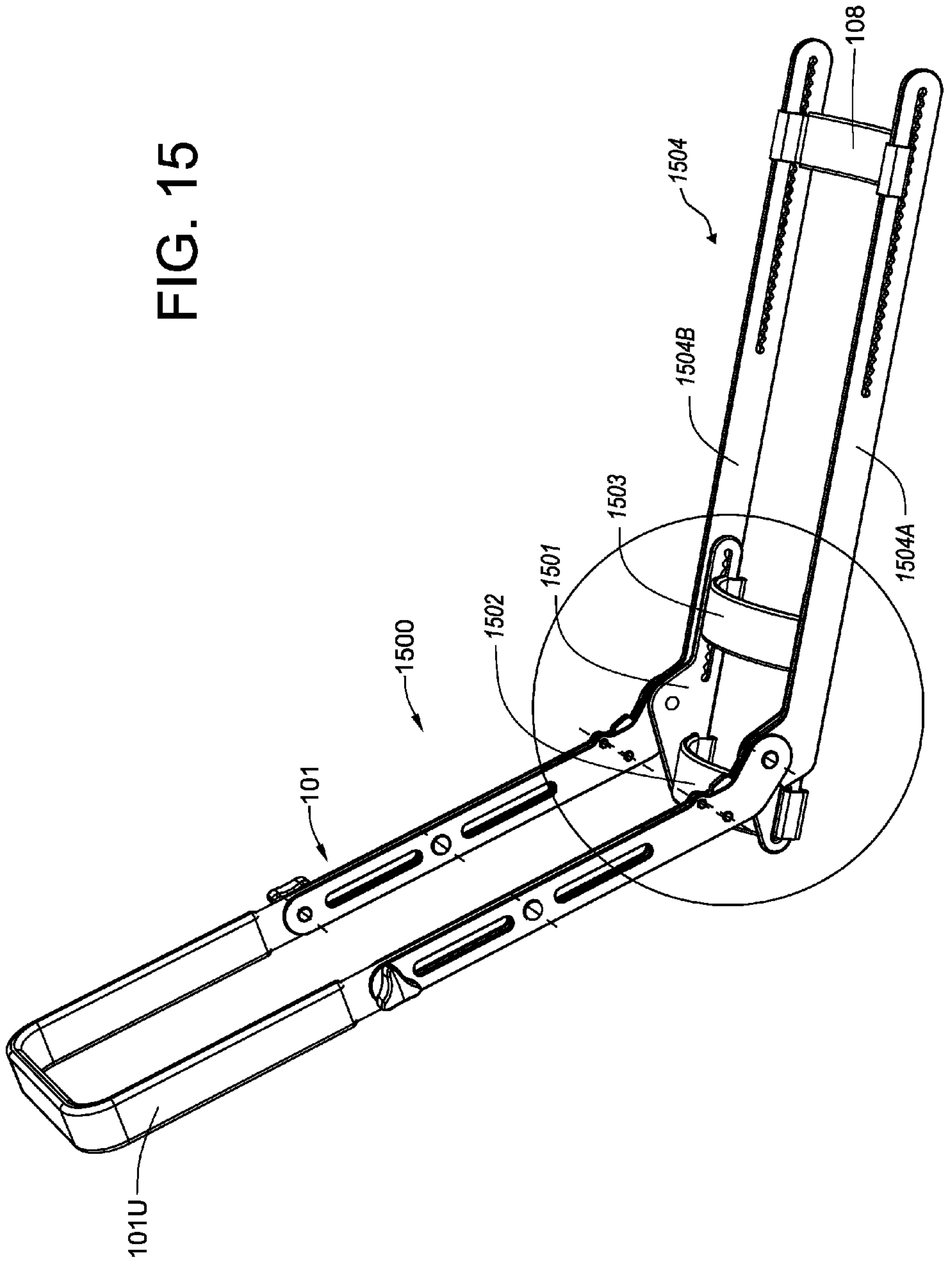
FIGS. 15, 16 and 17 show a second embodiment knee rehabilitation device in which the upper pair of knee bands are allowed to rotate independently of the ankle band, with each of the three figures showing a different degree of rotation.
Figure 16:
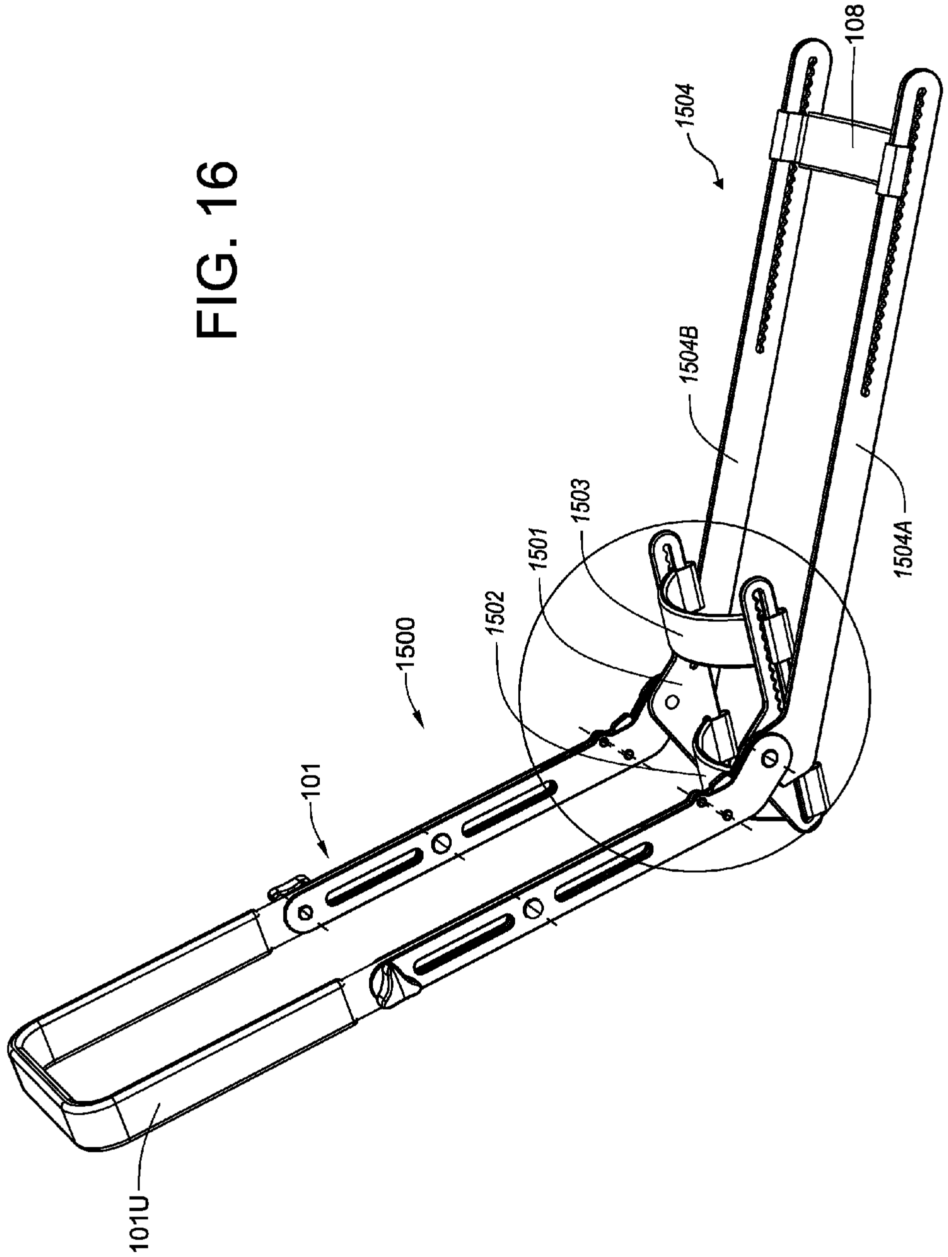
Figure 17:
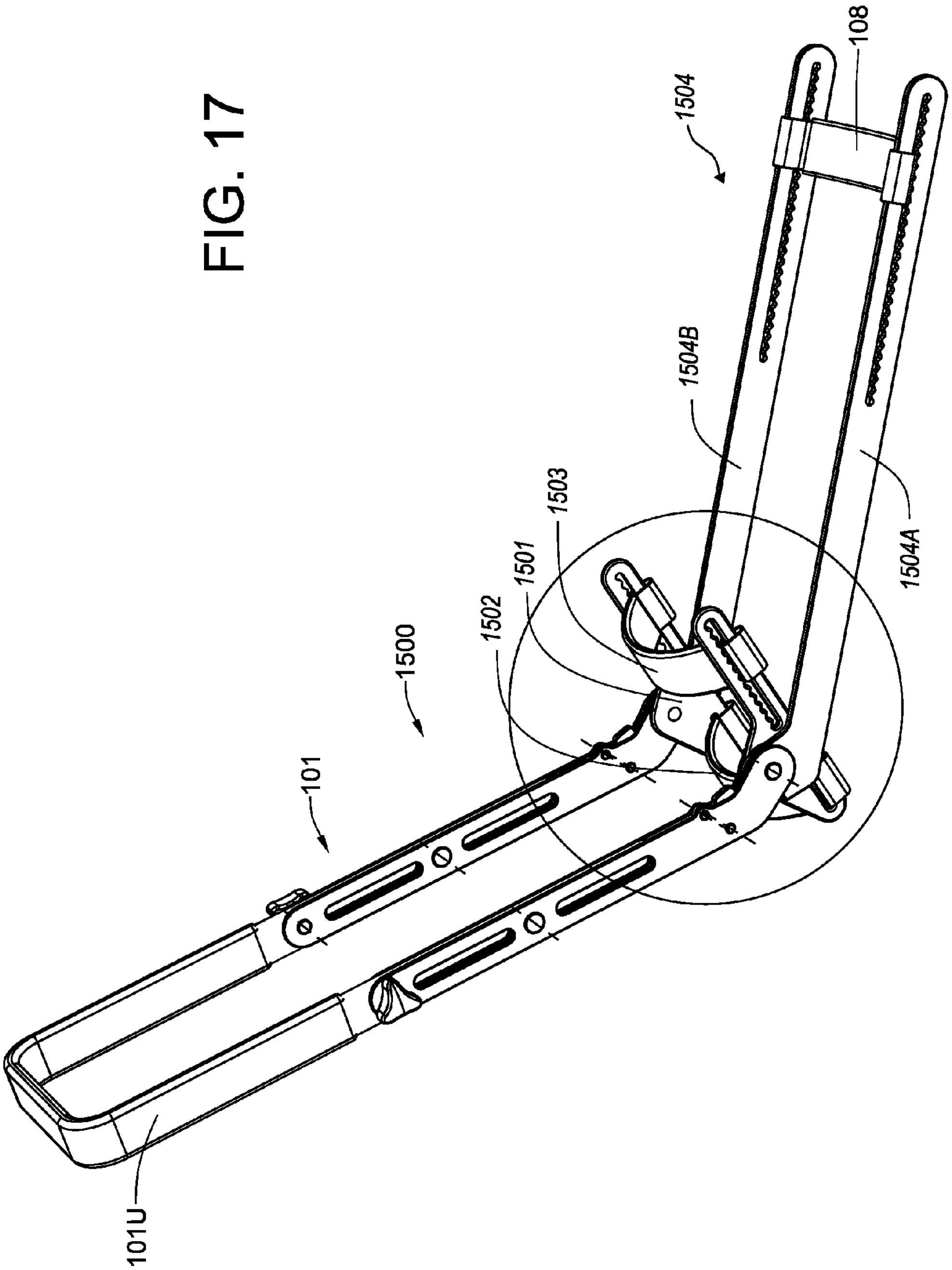

Referring now to FIGS. 15, 16 and 17, a second embodiment knee rehabilitation device 1500, which is a variation of the first embodiment knee rehabilitation device 100, incorporates a rotatable support structure 1501, to which the upper and middle bands 1502 and 1503, respectively, attach. The rotatable support structure 1501 enables the upper and middle bands 1502 and 1503 to rotate independently of the leg support 1504. FIGS. 15, 16 and 17 each show a different degree of rotation of the rotatable support structure 1501.

Figure 18:
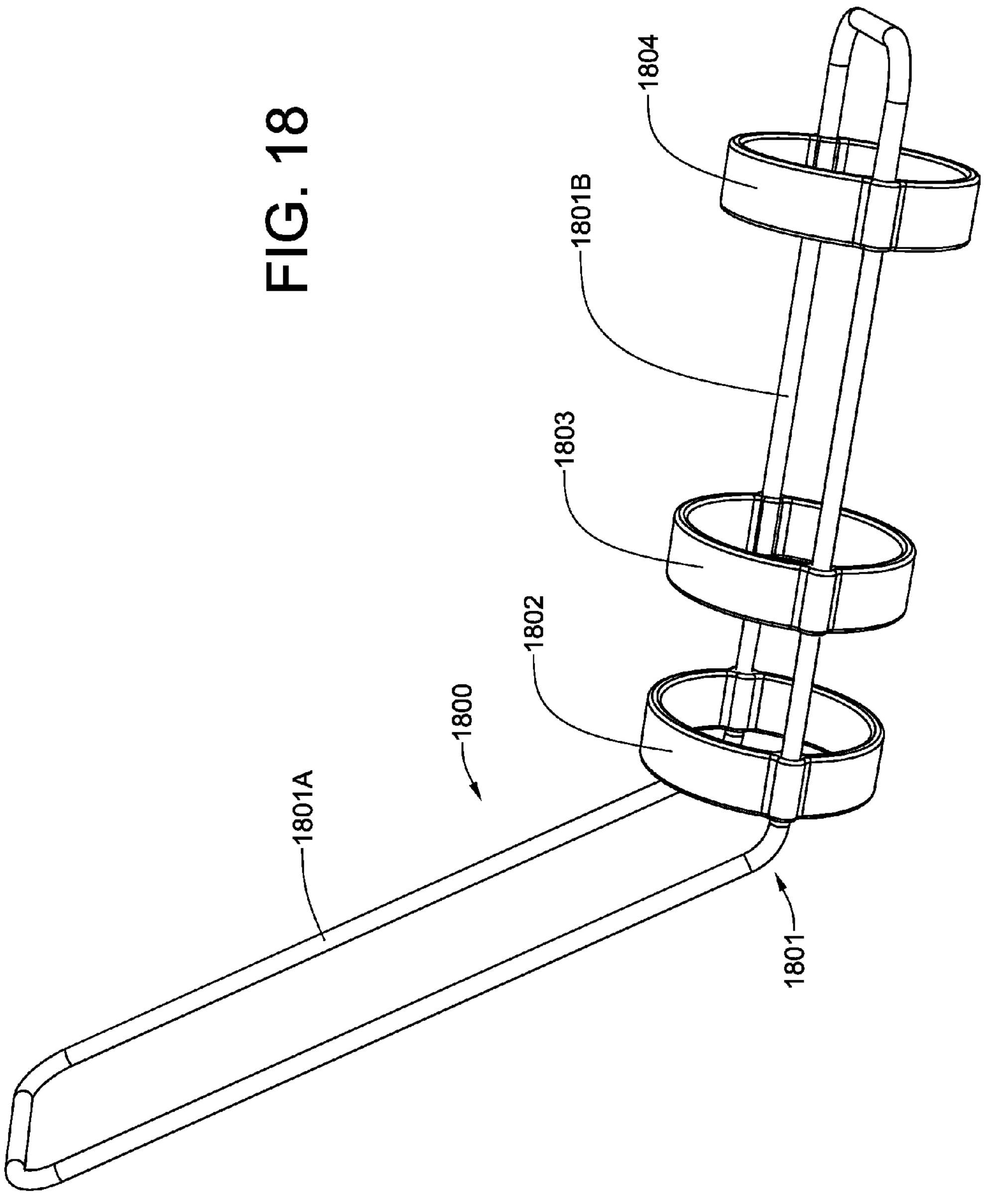
FIG. 18 is an isometric view from an upper right-side vantage point of a basic, less-expensive third embodiment knee rehabilitation device having a non-adjustable tubular frame and three slidable, adjustable s bands.
Figure 19:
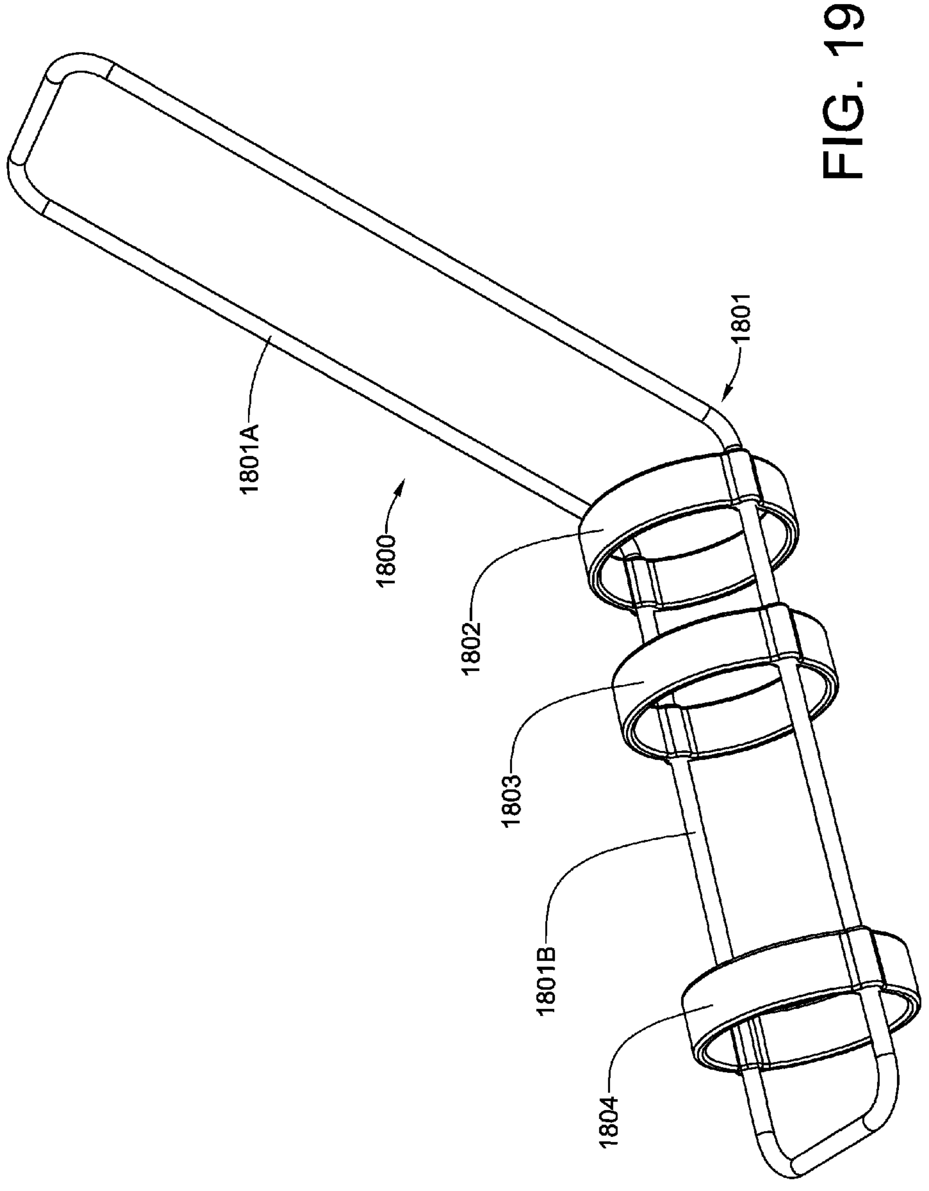
FIG. 19 is an isometric view from an upper-front, right-side vantage point of the third embodiment knee rehabilitation device.

Referring now to FIGS. 18 and 19, a third embodiment knee rehabilitation device 1800 has a non-adjustable tubular metal frame 1801 in which the handle portion 1801A is rigidly affixed to a leg support portion 1801B. An upper band 1802, a middle band 1803 and a lower band 1804 can be slidably positioned along the parallel tubes of the leg support portion 1801B.

Figure 20:
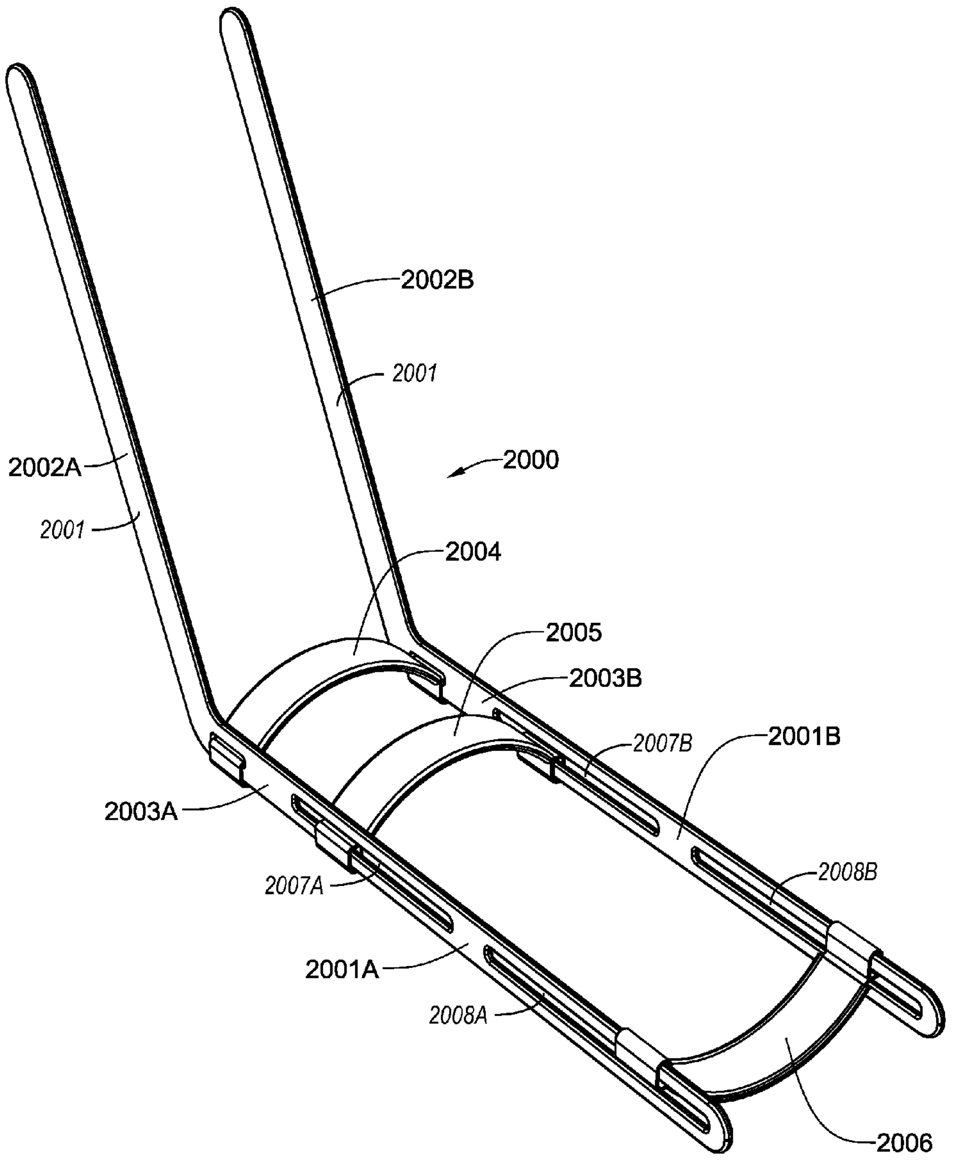
FIG. 20 is an isometric view from an upper-front, right-side vantage point of a fourth embodiment knee rehabilitation device having a non-adjustable frame made of laminar sheet material having a fixed upper band, and slidably movable middle and lower s bands.
Figure 21:
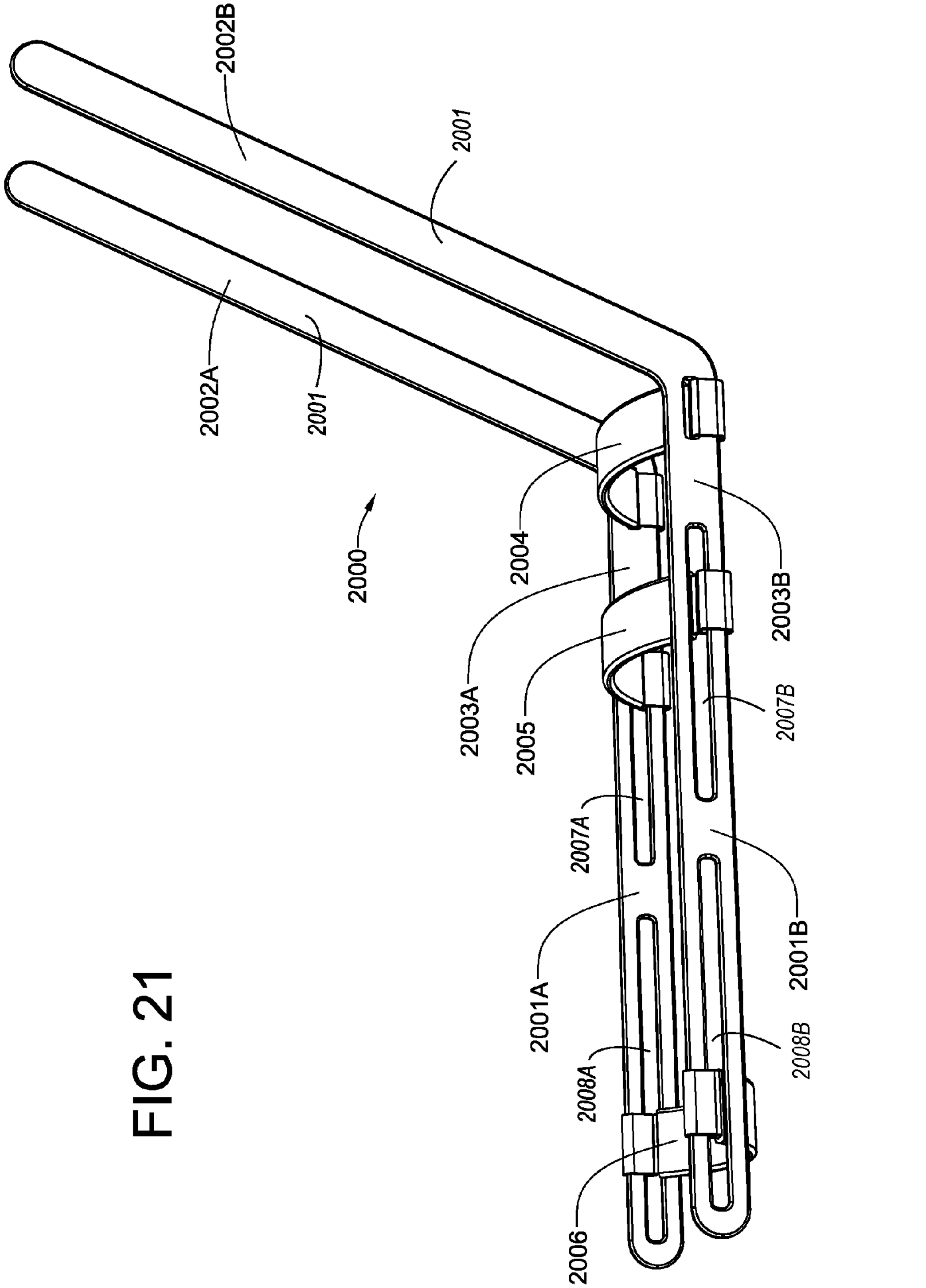
FIG. 21 is an isometric view from an upper-left vantage point of the fourth embodiment knee rehabilitation device.
Figure 22:
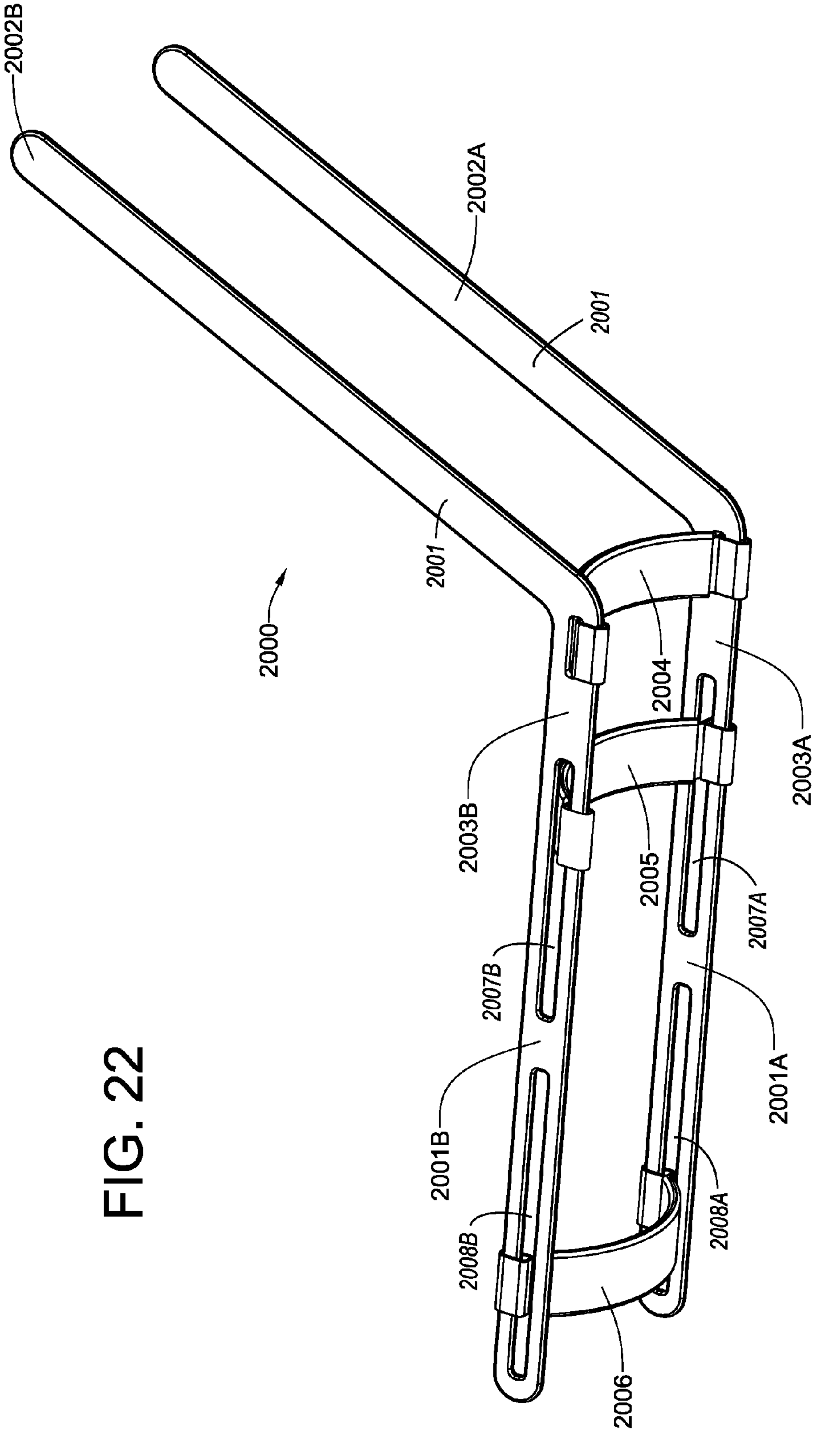
FIG. 22 is an isometric view from a lower-left rear vantage point of the fourth embodiment knee rehabilitation device.

Referring now to FIGS. 20, 21 and 22, a fourth embodiment knee rehabilitation device 2000 has a non-adjustable frame 2001 made of a pair of laminar sheet material components 2001A and 2001 B disposed in a mutually-parallel configuration. The laminar sheet material can be a structural metal such as aluminum, steel alloys, stainless steel alloys, magnesium alloys and titanium. It can also be a polymeric material, such as polyester thermoplastic resin that is reinforced by structural fibers such as para-aramid (e.g., Kevlar®), glass and carbon. Each of the frame components 2001A and 2001B is reminiscent of a hockey stick or boomerang, with a first end 2002A and 2002B of each serving as a handle and the other end 2003A and 2003B serving as half of the leg support portion. Front, middle and rear bands (2004, 2005 and 2006, respectively) bridge the gap between the two frame components 2001A and 2001B. Each frame component is equipped with a pair of longitudinal slots 2007A, 2008A and 2007B, 2008B, in the leg support portion 2003A/2003B, which enable the front and middle bands 2005 and 2006 to adjustably slide back and forth in order to accommodate different sizes of patients and different therapy positions.

Figure 23:
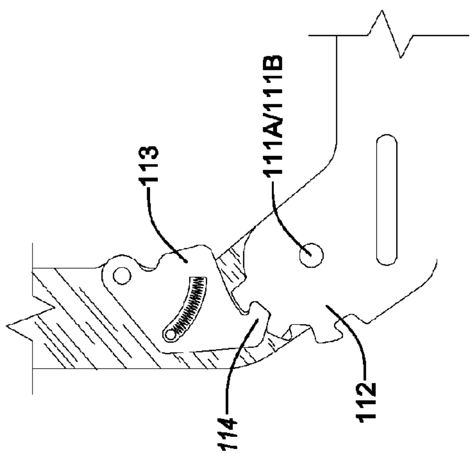
FIG. 23 is a cut-away drawing of the notched locking disc and pawl, with the pawl engaging the third notch of the locking disc.
Figure 26:
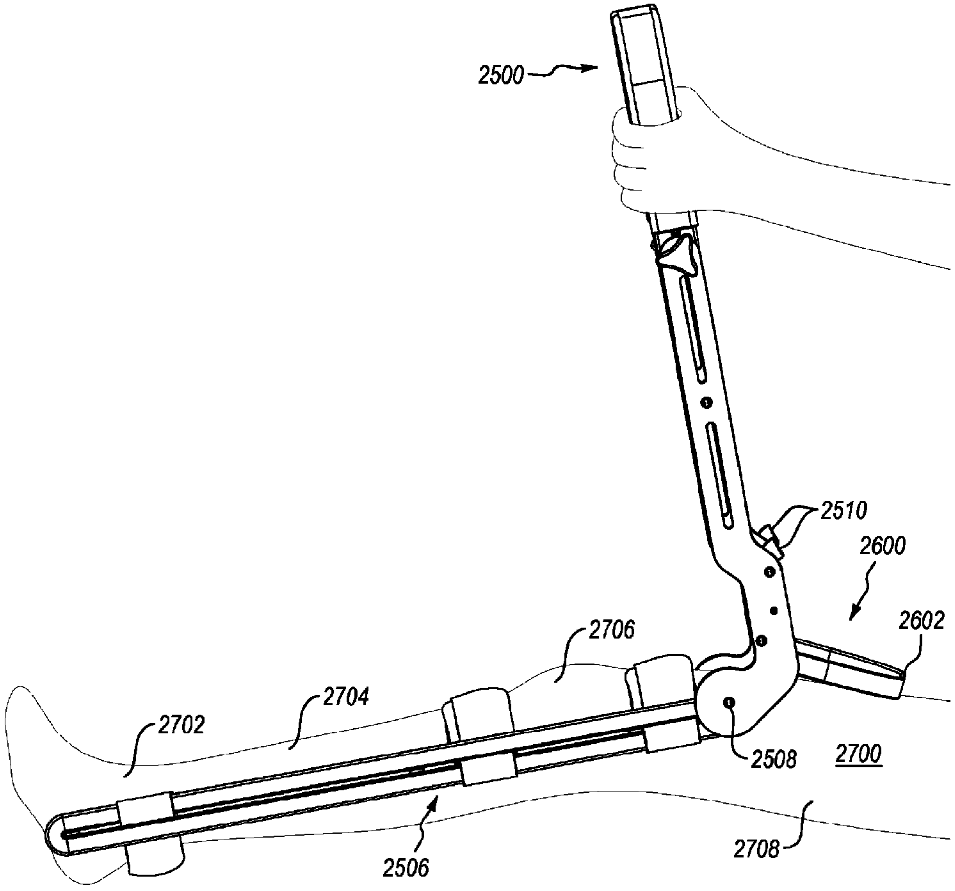
FIG. 26 is a side view of another embodiment of a knee rehabilitation device, with the knee rehabilitation device positioned for use in connection with the knee joint of a patient.

Referring now to FIG. 23, the notched locking disc 112 and pawl 114, with the pawl 114 engaging the third notch of the locking disc 112 are shown. The release button 113 is unitary with the pawl.

Figure 24:
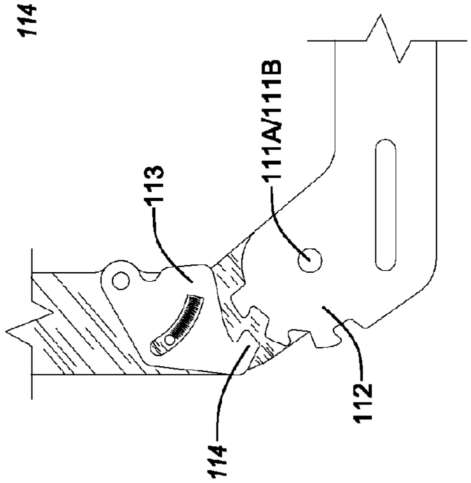
FIG. 24 is a cut-away drawing of the notched locking disc and pawl, with the pawl disengaged from the locking disc.

Referring now to FIG. 24, the release button 113 has been depressed, thereby disengaging the pawl 114 from the locking disc 112.

Figure 25:
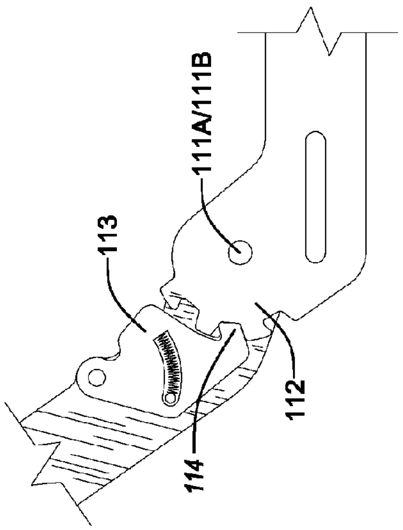
FIG. 25 is a cut-away drawing of the notched locking disc and pawl, with the pawl engaging the second notch of the locking disc.

Referring now to FIG. 25, the release button 113 has been allowed to spring back to its locked position, where the pawl 114 has engaged the second notch of the locking disc 112.

With reference now to FIGS. 26-30, details are provided concerning various general aspects of some alternative embodiments of a knee rehabilitation device, one of which is denoted generally at 2500. Except as may be noted in the following discussion and/or in FIGS. 26-30, the knee rehabilitation device 2500 may be similar, or identical, in structure and/or operation to any of the other embodiments of the knee rehabilitation device disclosed herein.

As indicated in FIGS. 26-30, the knee rehabilitation device 2500 may include a measurement device, one embodiment of which is denoted at 2600. In general, the measurement device 2600 is a mechanism that permits a therapist and/or patient to visually ascertain, and quantify, the extent to which the patient is able to flex his knee joint when using the knee rehabilitation device 2500.

Accordingly, the measurement device 2600 can be used to identify a baseline range of motion for a patient just beginning therapy, and the measurement device 2600 can also be used to help track the progress of the patient, in terms of changes in knee joint flexibility, over a period of time that may include multiple therapy sessions. For example, by using the measurement device 2600 to measure a range of motion of the knee joint on a periodic or other basis, a therapist can determine both the extent, and rate, of progress made by the patient.

As well, and discussed in more detail below, the measurement device 2600 can be integrated directly into the knee rehabilitation device and as a result, obviates the need for a separate measuring tool that could become lost or misplaced.

Further, the measurement device 2600 operates automatically without requiring patient or therapist involvement. In particular, the measurement device 2600 produces a measurement automatically as a result of the operation of the knee rehabilitation device and, as such, does not require a separate measuring step to be performed by the therapist or patient.

Additionally, accurate measurements can be taken very quickly with the measurement device 2600 without requiring the patient to maintain his knee in a particular position during the measurement process.

Moreover, because the measurement device 2600 is a relatively simple mechanism that includes no electronic elements, or fragile elements, it is very reliable and not prone to failures and malfunctions.

Figure 28:
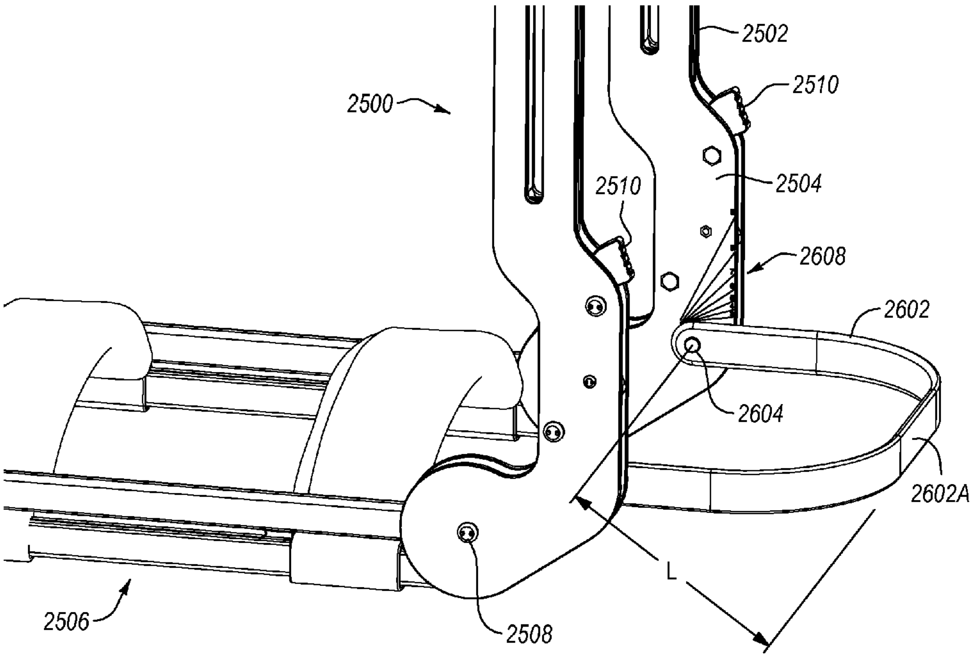
FIG. 28 is a detail perspective view that discloses aspects of an embodiment of a measurement device.
Figure 29:
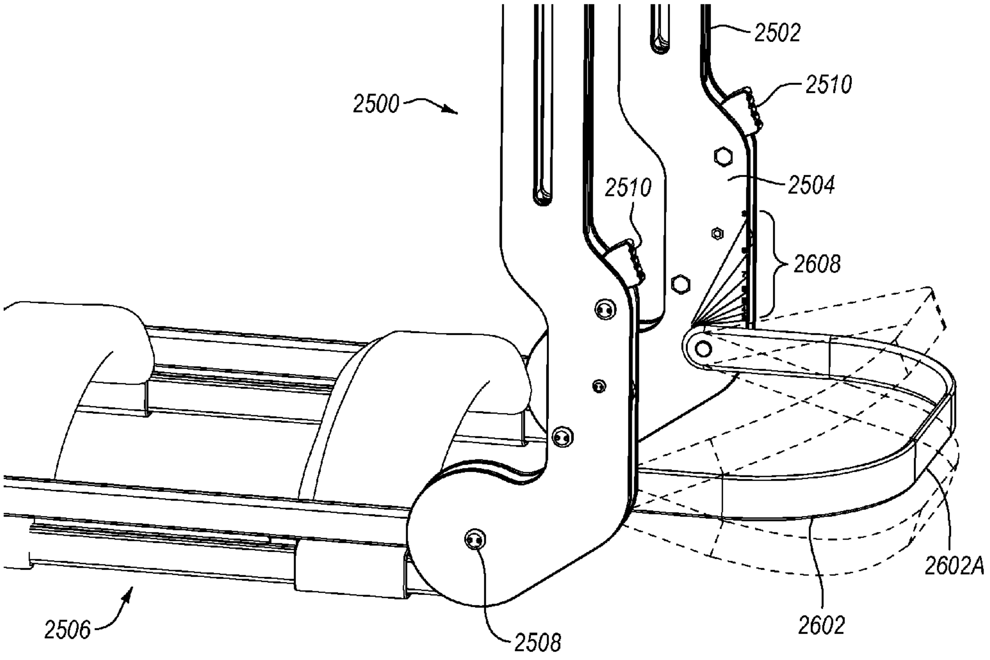
FIG. 29 is a detail perspective view that disclosed operational aspects of an embodiment of measurement device.
Figure 30:
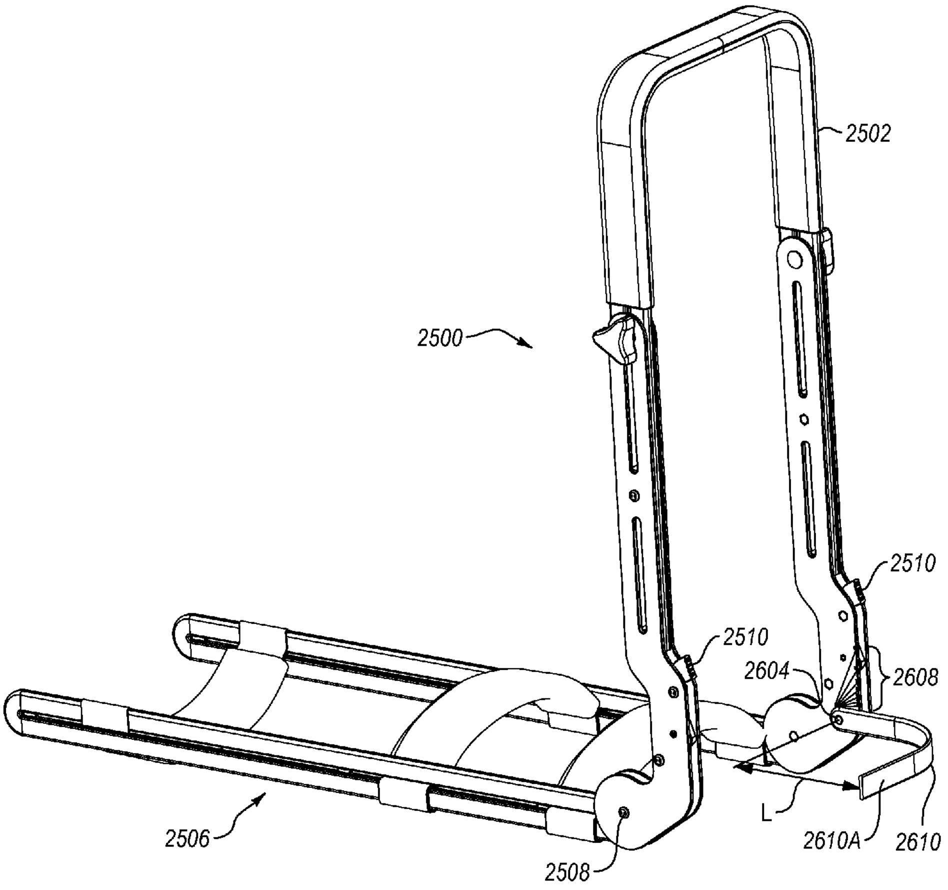
FIG. 30 is a detail perspective view of an alternative embodiment of a measurement element.

With more particular reference now to FIGS. 26-30, details are provided concerning the example measurement device 2600. In general, the measurement device 2600 may take the form of a measurement element 2602 that is rotatably attached to a portion of the knee rehabilitation device 2500. The measurement element 2602 can be made from any of a variety of materials, or combinations thereof, including, but not limited to, metals and plastics. In terms of its shape, the measurement element 2602 can take a variety of forms, including a generally U-shaped form as indicated in FIGS. 26-29, or a generally L-shaped form as indicated in FIG. 30.

More generally however, the measurement element 2602 can take any form that, by virtue of contact between a patient contact portion 2602A of the measurement element 2602 and the anatomy 2700 of the patient, enables displacement of the measurement element 2602 as a result of movement of the knee joint of the patient. In the example of FIGS. 26-29, the anatomy 2700 of the patient may include any one or more of, the ankle 2702, lower leg 2704, knee joint 2706, or thigh 2708 of the patient.

Figure 27:
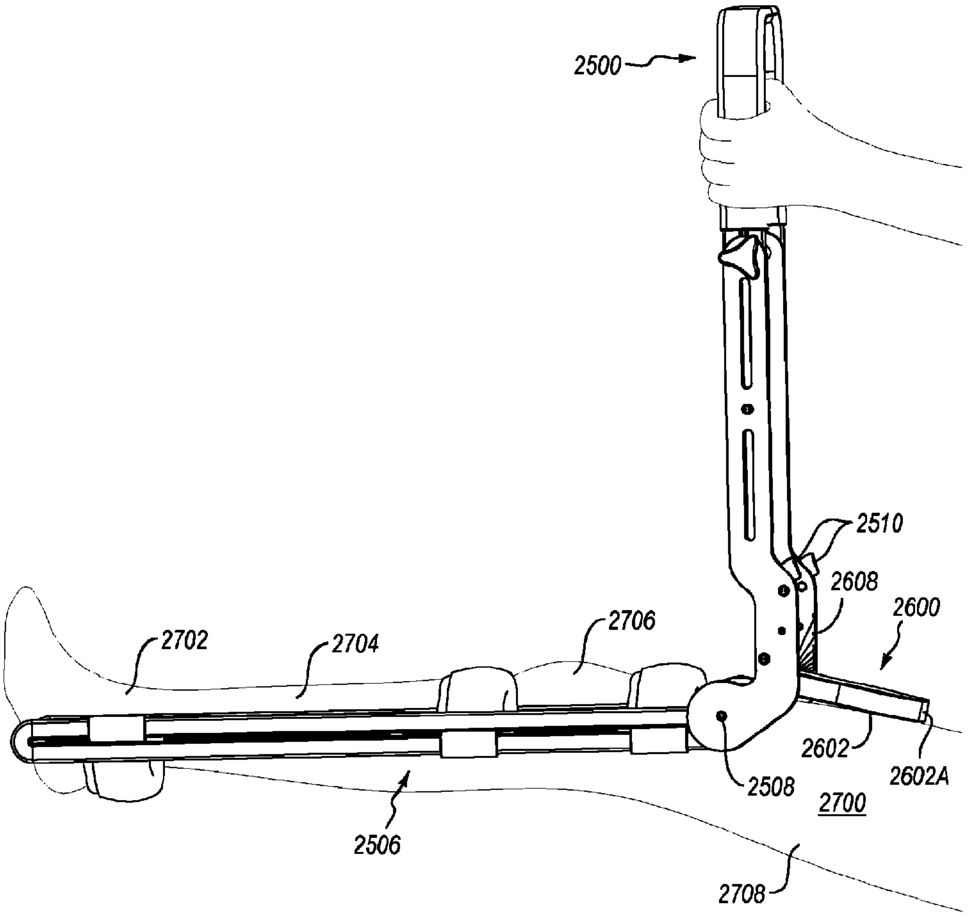
FIG. 27 is another side view of another embodiment of a knee rehabilitation device, with the knee rehabilitation device positioned for use in connection with the knee joint of a patient.

The measurement element 2602 should, when positioned in a generally horizontal orientation, indicated in FIG. 27 for example, extend outwardly from the handle 2502 a sufficient distance "L" (see, e.g., FIGS. 28 and 30) that the extent to which a patient is able to flex his knee joint can be readily recorded by the measurement element 2602. It can be appreciated from the Figures that if the measurement element 2602 does not extend outwardly a sufficient distance, it may be difficult to ascertain the flexibility of the knee joint of the patient because even a large rotation of the knee joint will cause only a small displacement of the measurement element 2602. In general, the further that the measurement element 2602 extends away from the handle 2502, the greater the sensitivity of the measurement element 2602 to a rotation of the knee joint of the patient. Thus, for example, where only small changes are expected in the extent to which a patient is able to rotate his knee, a relatively long "L" dimension may be desirable.

In the illustrated examples, the measurement element 2602 is attached to one or both of the interior sides 2504 of the handle 2502 of the knee rehabilitation device 2500 by way of a pin 2604 or comparable element such as a rivet, screw or bolt, for example. As a result of this attachment, the measurement element 2602 is able to rotate relative to the handle 2502. Thus, even if the angle of the handle 2502 relative to the leg support 2506 is changed, such as to suit some therapeutic need, the measurement element 2602 can be repositioned, relative to the handle 2502, as necessary to enable the desired measurement(s) concerning the range of motion of the knee joint 2706 to be obtained.

It should be noted that the specific location of attachment of the measurement element 2602 to the handle 2502 shown in the Figures is presented by way of example only and is not intended to limit the scope of the invention in any way. More generally, the measurement element 2602 can be attached to the knee rehabilitation device 2500 at any location that enables the measurement functionality disclosed herein. For example, the measurement element 2602 can be attached to the knee rehabilitation device 2500 by the same pin 2508 or other mechanism(s) that are used to attach the handle 2502 to the leg support 2506. Finally, the pin 2604 and/or other element(s) used to attach the measurement element 2602 to the handle 2502, or other portion of the knee rehabilitation device 2500, may be configured such that the measurement element 2602 tends to remain in whatever position it is rotated to, until it is subsequently moved.

With particular reference to the example of FIG. 29, the measurement element 2602 may have a defined range of rotational motion, indicated by the various example positions of the measurement element 2602 illustrated in FIG. 29. In one example embodiment, the total range of rotational motion of the measurement element 2602 is about 90 degrees, namely from a zero degree substantially horizontal position to a 90 degree substantially vertical position. In some embodiments, the rotational range of motion may be less than about 90 degrees, or greater than about 90 degrees. In yet other embodiments, the measurement element 2602 may be substantially unrestrained in terms of its rotational motion, such that it can rotate in a range of about 300 degrees to about 360 degrees. In general, the range of motion can be selected and implemented based upon the range of motion expected to be experienced by the knee rehabilitation device 2500 and, particularly, the range of motion of the handle 2502.

With continued reference to FIG. 29, and directing particular attention to FIG. 28, the measurement device 2600 further comprises a scale 2608, which can be inscribed, painted or otherwise formed, that enables a patient and/or therapist to visually determine a relative displacement of the measurement element 2602, such as may occur during a therapy session. In general, the scale 2608 corresponds to a range of motion, of a knee joint of a patient for example. The scale 2608 may, but need not, indicate an actual angle of inclination of the measurement element 2602 relative to the handle 2502. Alternatively, the scale 2608 may, as shown in the example of FIG. 29, simply include a set of numbers and/or lines or other indicators or markers that indicate different respective amounts of relative inclination. In the example of FIG. 29, and FIG. 30 discussed below, the scale 2608 includes a series of lines that indicate progressively greater inclination of the measurement element 2602 relative to the handle 2502 which, thus, correspond to progressively greater range of motion of the knee joint of a patient using the knee rehabilitation device 2500.

Turning now to FIG. 30, details are provided concerning an alternative embodiment of the measurement element, denoted at 2610. In terms of its materials and operation, the measurement element 2610 is similar, or identical, to the measurement element 2602.

As indicated in FIG. 30, the measurement element 2610 is generally L-shaped and includes a patient contact portion 2610A. The measurement element 2610 can be attached to either side of the handle 2502 in the same manner noted above in the discussion of measurement element 2602. The side of the handle 2502 to which the measurement element 2610 is attached includes a scale 2608, discussed above.

With brief continuing reference to FIGS. 26-30, the knee rehabilitation device 2500 may include, in addition to the measurement device 2600, release buttons 2510 and associated components similar, or identical, in structure and operation to the release buttons 113 and associated components disclosed in FIGS. 23-25. The embodiment of FIGS. 26-30 differs however from that of FIGS. 23-25 in that in the latter embodiment, the release buttons 113 are located on the side of the handle positioned away from the patient, while in the former embodiment, the release buttons 2510 on located on the side of the handle 2502 nearest the patient.

Figure 31:
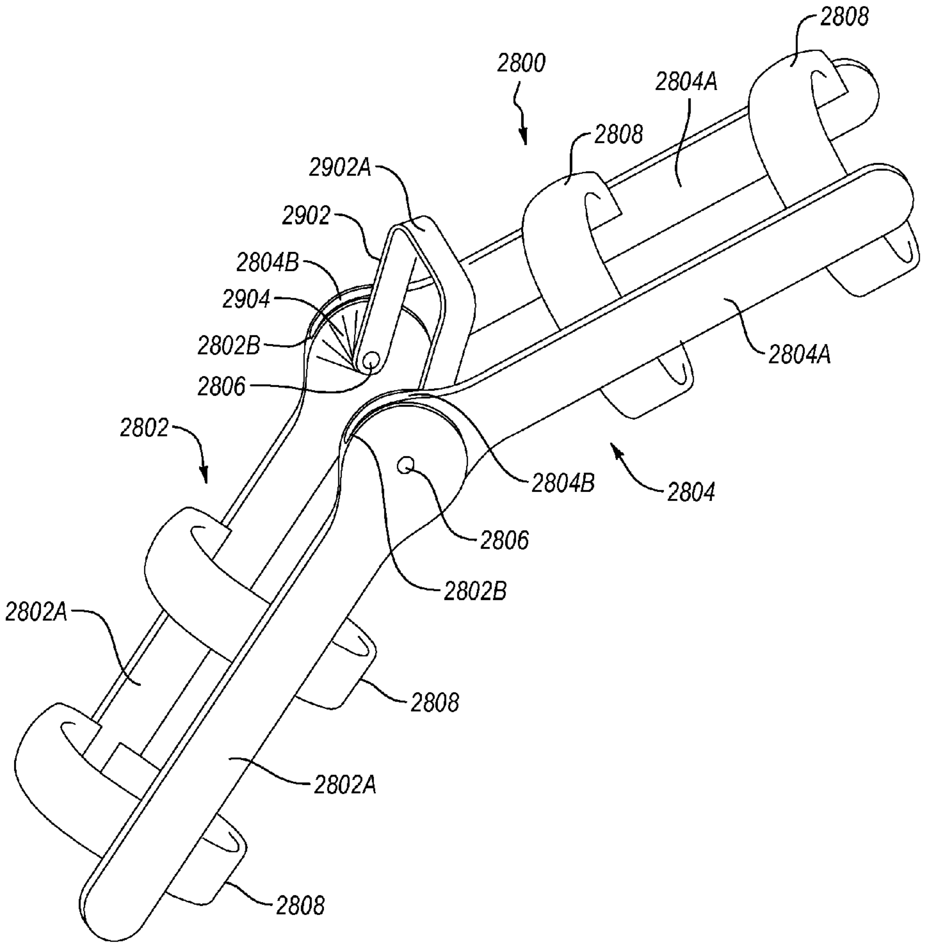
FIG. 31 is a perspective view of a therapy device that includes a measurement device.

Turning now to FIG. 31, details are provided concerning a therapy device, one example of which is denoted at 2800. The therapy device 2800 can be any contracture correction device, and is not limited to the examples disclosed herein. In one particular example embodiment, the therapy device 2800 is a flexion contracture correction (FCC) device that can be used on a knee joint and/or other joints. The therapy device 2800 may also take the form of a dynamic splint, or comparable devices.

Except as may be noted in the following discussion and/or in FIG. 31, the therapy device 2800 may, in some embodiments, be similar, or identical, in structure and/or operation to any of the embodiments of the knee rehabilitation device disclosed herein.

The therapy device 2800 in this example includes a first support 2802 rotatably connected to a second support 2804 by way of pins 2806 or comparable structures. In the example of FIG. 31, the first support 2802 includes a set of elongate members 2802A, each of which defines a slot 2802B at its proximal end which is configured to at least partly receive a corresponding terminal portion 2804B located at a distal end of the elongate members 2804A. Except in the aforementioned respects concerning slots 2802B and terminal portions 2804B, the elongate members 2802A/B and 2804A/B may be similar or identical, in structure and/or operation, to other example elongate members disclosed herein.

Alternatively, the first support 2802 and/or second support 2804 may each include respective sets of elongate members 2802A/B and 2804A/B that may be similar or identical, in structure and/or operation, to other example elongate members disclosed herein. By way of example, any one or more of the elongate members 2802A/B and 2804A/B may define slots (not shown) to which one or more bands 2808, examples of which are disclosed herein, may be permanently or releasably connected.

In at least some embodiments, the elongate members 2802A/B may be spring-loaded, or otherwise biased, so as to have a tendency to rotate in a clockwise or counter-clockwise direction (as viewed from the perspective of FIG. 31) relative to elongate members 2804A/B. Alternatively, the elongate members 2802A/B may be spring-loaded, or otherwise biased, so as to have a tendency to rotate in a clockwise or counter-clockwise direction (as viewed from the perspective of FIG. 31) relative to elongate members 2804A/B. Either of these spring-loaded configurations may be employed where the therapy device 2800 is an FCC device.

Finally, the therapy device 2800, in any of the disclosed forms, may include a measurement device 2900 that may be similar, or identical, in structure and/or operation to other embodiments of measurement devices disclosed herein. The example measurement device 2900 includes a generally U-shaped measurement element 2902 that has a patient contact portion 2902A. A scale 2904 enables a therapist and/or patient to ascertain the extent to which a joint has been rotated with the therapy device 2800.

Returning attention now to FIG. 27 in particular, details concerning the operation of the measurement device 2600 of FIGS. 26-30 are provided. Initially, the knee rehabilitation device 2500 is attached to the leg of the patient and may be positioned as indicated in FIG. 27, with the leg of the patient in a generally horizontal disposition. Alternatively, the leg of the patient may be oriented such that the knee is in a substantially unrotated disposition where the lower leg 2704 is generally perpendicular to the thigh 2708. The foregoing are presented solely by way of example however, and other leg positions can be employed.

After the knee rehabilitation device 2500 is attached to the leg of the patient, the position of the handle 2502 relative to the leg support 2506 can be adjusted, if desired. When the handle 2502 is in position and prior to the beginning of therapy, in the form of knee rotation for example, the measurement element 2602 is rotated downward into contact with the anatomy 2700 of the patient, such as the thigh 2708 for example.

After the measurement element 2602 has been thus positioned, the handle 2502 can be rotated (clockwise in FIG. 27) toward the user to effect rotation of the knee joint. Because the measurement element 2602 is prevented from rotating in the same direction by virtue of its contact with the anatomy 2700 of the patient, the handle 2502 rotates relative to the measurement element 2602. When rotation of the knee joint has been completed and the handle 2502 is released, the measurement element 2602 maintains its position relative to the handle 2502, thereby indicating on the scale 2608 the extent of the relative motion between the handle 2502 and the measurement element 2602. Because movement of the handle 2502 corresponds to an extent of rotation of the knee joint of the patient, the positions of the handle 2502 and measurement element 2602 relative to each other indicate the extent to which the knee joint of the patient has been rotated. Thus, measurement of the extent of rotation, either in relative or actual terms, is obtained automatically, without any action by the therapist or patient other than rotation of the knee joint, as a result of the operation of the knee rehabilitation device 2500 and, particularly, the relative motion between the handle 2502 and measurement element 2602.

Since the measurement element 2602 tends to maintain its position relative to the handle 2502, the therapist and/or patient can quickly visually ascertain the extent to which the knee joint was rotated by simply observing the position of the measurement element 2602 on the scale 2608. Moreover, because the measurement is taken simultaneously, and automatically, with rotation of the knee joint by the knee rehabilitation device 2500, the patient is not required to maintain the knee joint in position while waiting for a measurement to be taken.

As will be apparent from the discussion herein, embodiments of the measurement device, such as measurement device 2600 for example, constitute example structural implementations of a means for measuring joint rotation. As such, these means serve to implement any one or more of the various functions ascribed herein to one or more embodiments of the measurement device.

Although this disclosure has been described in terms of certain embodiments, other embodiments apparent to those of ordinary skill in the art are also within the scope of this disclosure. Accordingly, the scope of the disclosure is intended to be defined only by the claims which follow.

What is claimed is:

1. A rehabilitation device, comprising:

a first element having first and second spaced-apart, generally parallel elongate members having proximal and distal ends, and a first band suspended between the elongate members;

a second element rotatably coupled to the first element and having first and second spaced-apart, generally parallel elongate members having proximal and distal ends, and wherein one of the first and second elements is angularly adjustable relative to the other of the first and second elements; and a measurement device, comprising:

a measurement element connected to one of the first and second elements and configured for rotation relative to one of the first and second elements, wherein when the rehabilitation device is operably disposed with respect to a joint that connects first and second portions of a limb of a patient, the measurement element extends laterally across part of the first portion of the limb of the patient, wherein an angular displacement of the measurement element indicates the extent to which the second portion of the limb has rotated relative to the first portion of the limb, and wherein the measurement element is configured such that, after rotation of the second portion of the limb has ceased, the measurement element maintains its displaced position and continues to visually indicate the extent to which the second portion of the limb has rotated; and a scale disposed proximate the measurement element and indicating a position of the measurement element relative to another portion of the rehabilitation device.

2. The rehabilitation device as recited in claim 1, wherein the first and second elements are rotatably coupled to each other by way of an angularly-adjustable coupler, wherein the angularly-adjustable coupler is operable to implement variations to an angle cooperatively defined by the first and second elements, and the angularly-adjustable coupler including a locking mechanism operable to releasably lock the first and second elements at a plurality of different angular positions relative to each other.

3. The rehabilitation device as recited in claim 1, wherein the measurement element has a range of motion of at least about 90 degrees.

4. The rehabilitation device as recited in claim 1, wherein following a rotation of the second portion of the limb, the measurement element cooperates with the scale to visually indicate the angular measurement of the extent to which the second portion of the limb was rotated.

5. The rehabilitation device as recited in claim 4, wherein the visual indication of the maximum extent to which the second portion of the limb has been rotated occurs automatically as a result of operation of the rehabilitation device.

6. The rehabilitation device as recited in claim 4, wherein the visual indication of the maximum extent to which the second portion of the limb has been rotated occurs simultaneously with operation of the rehabilitation device.

7. The rehabilitation device as recited in claim 1, wherein the joint is a knee joint.

8. The rehabilitation device of claim 1, wherein the first and second elements are rotatably coupled together such that a proximal end of the first element is coupled to a distal end of the second element.

9. The rehabilitation device of claim 1, further comprising one or more additional bands suspended either between the first and second spaced-apart, generally parallel elongate members of the first element, or between the first and second spaced-apart, generally parallel elongate members of the second element.

10. The rehabilitation device of claim 1, wherein the first element comprises a fixed length leg support having first and second spaced-apart, generally parallel elongate members having proximal and distal ends, an ankle band suspended between said elongate members, wherein a position of the ankle band relative to the distal ends of the elongate members is adjustable, and an over-front-of-the-leg band suspended between said elongate members near the proximal ends thereof, wherein a position of the over-front-of-the-leg band relative to the proximal ends of the elongate members is fixed.

11. The rehabilitation device of claim 1, wherein the second element comprises a handle rotatably coupled to the proximal ends of the elongate members of the first element.

12. A rehabilitation device, comprising:

a leg support having first and second spaced-apart, generally parallel elongate members having proximal and distal ends, and a first band suspended between the elongate members;

a handle having a first end rotatably coupled to the proximal ends of the elongate members, and the handle having a free second end that, in use, is rotatable to impart a rotation to a lower leg of a patient;

an angularly-adjustable coupler by way of which the handle is rotatably coupled to the leg support, wherein the angularly-adjustable coupler is operable to implement variations to an angle cooperatively defined by the handle and the leg support, and the angularly-adjustable coupler including a locking mechanism operable to releasably lock the handle at a plurality of different angular positions relative to the leg support; and a measurement device that comprises:

a measurement element rotatably connected to the handle, wherein when the rehabilitation device is operably disposed with respect to a knee joint of the patient, the measurement element extends laterally across part of the upper leg of the patient, wherein an angular displacement of the measurement element indicates the extent to which the lower leg of the patient has rotated relative to the upper leg, and wherein the measurement element is configured such that after rotation of the lower leg has ceased, the measurement element maintains its displaced position and continues to visually indicate the extent to which the lower leg has rotated; and a scale located proximate the measurement element.

13. The rehabilitation device of claim 12, wherein the measurement element is configured and arranged such that when the rehabilitation device is operably disposed with respect to the knee joint of a patient, the measurement element is movable into, and out of, contact with the upper leg of the patient.

14. The rehabilitation device of claim 12, wherein the measurement device is configured either:

substantially in the shape of a "U" and connected to the handle such that when the rehabilitation device is operably disposed with respect to the knee joint, the measurement element straddles the upper leg of the patient; or substantially in the shape of an "L" such that when the rehabilitation device is operably disposed with respect to the knee joint, a free end of the measurement element extends partway across the upper leg of the patient.

15. The rehabilitation device of claim 12, wherein movement of the lower leg of the patient toward an extended position corresponds with a rotation of the handle toward the patient.

16. The rehabilitation device of claim 12, further comprising:

an ankle band suspended between the elongate members and configured to be positioned behind the leg of the patient proximate an ankle of the patient; and an over-front-of-the-leg band suspended between the elongate members near the proximal ends.

17. The rehabilitation device of claim 12, wherein the scale is marked on the handle.

18. The rehabilitation device of claim 12, wherein a length of the handle is adjustable.

19. A flexion contracture correction (FCC) device, comprising:

a first leg support having first and second spaced-apart, generally parallel elongate members having proximal and distal ends, and one or more bands suspended between the elongate members, and the first leg support having a proximal end and a distal end;

a second leg support rotatably connected to the first leg support and having first and second spaced-apart, generally parallel elongate members having proximal and distal ends, and one or more bands suspended between the elongate members of the second leg support, and the second leg support having a proximal end and a distal end, wherein the distal end of the second leg support is rotatably connected to the proximal end of the first leg support; and a measurement device, comprising:

a measurement element rotatably connected to one of the leg supports and configured for rotation relative to that leg support, wherein when the FCC device is operably disposed with respect to a knee joint of a patient, the measurement element extends across part of an upper leg of the patient, and an angular displacement of the measurement element indicates the extent to which a lower leg of the patient has rotated relative to the upper leg of the patient, and wherein the measurement element is configured such that after rotation of the lower leg has ceased, the measurement element maintains its displaced position and continues to visually indicate the extent to which the lower leg has rotated; and a scale disposed proximate the measurement element and indicating a position of the measurement element relative to the leg support to which the measurement element is attached.

20. The FCC device as recited in claim 19, wherein the measurement element is either substantially in the shape of a "U," or substantially in the shape of an "L".

21. The FCC device as recited in claim 19, wherein following a rotation of the lower leg by the FCC device, the measurement element cooperates with the scale to visually indicate the angular measurement of the extent to which the lower leg was rotated.

22. The FCC device as recited in claim 21, wherein the visual indication of the maximum extent to which the lower leg has been rotated occurs automatically as a result of operation of the FCC device.

23. The FCC device as recited in claim 21, wherein the visual indication of the maximum extent to which the lower leg has been rotated occurs simultaneously with operation of the FCC device.

24. The FCC device as recited in claim 19, wherein one of the leg supports is biased to rotate in a particular direction relative to the other leg support.

25. The rehabilitation device as recited in claim 1, wherein the measurement element is either substantially in the shape of a "U," or substantially in the shape of an "L".

* * * * *